United States Patent
Hayashi et al.

(10) Patent No.: US 6,710,062 B1
(45) Date of Patent: Mar. 23, 2004

(54) CYANOMETHYLENE COMPOUNDS, PROCESS FOR PRODUCING THE SAME, AND AGRICULTURAL OR HORTICULTURAL BACTERICIDE

(75) Inventors: Masatoshi Hayashi, Naruto (JP); Yasuhiro Endo, Naruto (JP); Tomozo Komura, Naruto (JP)

(73) Assignee: Otsuka Chemical Co., Ltd., Osaka (JP)

(*) Notice: Subject to any disclaimer, the term of this patent is extended or adjusted under 35 U.S.C. 154(b) by 40 days.

(21) Appl. No.: 10/149,437

(22) PCT Filed: Sep. 5, 2000

(86) PCT No.: PCT/JP00/06001
§ 371 (c)(1),
(2), (4) Date: Jun. 24, 2002

(87) PCT Pub. No.: WO01/47902
PCT Pub. Date: Jul. 5, 2001

(30) Foreign Application Priority Data

Dec. 24, 1999 (JP) .............................. 11-367615

(51) Int. Cl.⁷ ................ C07D 277/10; A01N 43/78
(52) U.S. Cl. ................ 514/342; 514/365; 546/269.7; 548/146
(58) Field of Search ................ 514/342, 365; 546/269.7; 548/146

(56) References Cited

FOREIGN PATENT DOCUMENTS

| DE | 227705 A1 | 9/1985 |
| DE | 240544 A1 | 11/1986 |
| DE | 3803783 A1 | 8/1989 |
| EP | 842931 A1 | 5/1998 |
| JP | 54-122271 A | 9/1979 |

OTHER PUBLICATIONS

Rudorf, W.D. et al. "Kurze Originalmitteilungen–Die Reaktion von N,N–Dimethyl–hydrazonen mit Schwefelchloriden–eine einfache Synthese von 1,3,4–Thiakiazol–2(3h)–thionen", Z. Chem., 25(9), pp. 323–324 (1985).
Hanefeld, W. et al. "Cyclic Ketene–S, N–acetales from Iminium Thiocarbonic Acid Ester Chloride–Chloride and Doubly Activated Methylene Compound", Arch. Pharm. (Weinheim), 322, pp. 593–597 (1989).
Uhlig, G., et al., "Thiocarbamoylation of CH–Acid Arylsulfinyl and Arylthio Compounds", J. Prakt. Chem., 337, pp. 29–33 (1995).
Hanefeld, W. et al., "Imunium Carbonic Acid Derivative Salts. VIII[1]. Electrophilic Reactions of 2–Methylthio–5, 6–dihydro–1, 3–thiazinium Iodides, 2–Methylthio–5,6–dihydrothiazolium Iodides and 5–Methyl–2–methyl–thiothiazolium Iodides. Part II. With Active Methylene Compounds", J. Herocyclic Chem., 34, pp. 1621–1624 (1997).

Neplyuev, V. M., et al. "Arylsulfonylacetonitrile series. II. Cyclization of arylamides of arylsulfonylcyanothioacetic acid", Khim. Gaterotsiki. Soedin., (9), pp. 1194–1197 (1970).

Kleinpeter, E. et al. "Studies of the π–Electron Distribution in Push–Pull Alkenes by ¹H and ¹³C NMR Spectroscopy–II", Magn. Reson. Chem., 31, p. 714–721 (1993).

Mehta, M. R., et al. "Synthesis of 2,3–disubstituted–4–thiazolidinones and 3,5–diaminothiophene–2–carboxylic acid derivatives", Indian J. Chem. Sec. B, 29B, pp. 1146–1153 (1990).

Bukowski, L. et al., "Some reactions of 2–cyanomethylimidazo [4,5–b]pydidine with isothiocyanates. Antituberculotic activity of the obtained compounds", Pharmazie, 53., pp. 373–376 (1998).

Rudorf, W. D., "Heterocyclensynthesen Mit o–chlorbenzoyl–acetonitril", Tetrahedron, 34, pp. 725–730 (1998).

Rudorf, W. D., et al. "Reaction of o–Halobenzyl cyanides with Carbon Disulfide and Phenyl Isothiocyanate", Journal f. prakt. Chemie. vol. 321, pp. 1021–1028 (1979).

Hosomi, Akira et al., "N–(Silylmethyl)–Substituted Ketene N,S–Acetals as a Synthetic Equivalent of Novel 1,3–Dipolar Reagent, Alkylideneazomethine Ylids: Synthesis and [3+2] Cycloadditions", J. Org. Chem., 55, pp. 5308–5310 (1990).

Primary Examiner—Joseph K. McKane
Assistant Examiner—Kamal Saeed
(74) Attorney, Agent, or Firm—Armstrong, Kratz, Quintos, Hanson & Brooks, LLP

(57) ABSTRACT

The cyanomethylene compound of the invention is a compound represented by the formula (1)

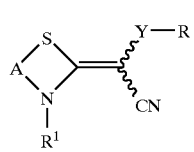

(1)

wherein R is $C_{1-20}$ straight-chain or branched-chain alkyl, $C_{3-8}$ cycloalkyl, aryl or heterocyclic group; and the aryl and the heterocyclic group may be substituted with one or more substltuents); $R^1$ is $C_{1-8}$ straight-chain or branched-chain alkyl, $C_{3-8}$ cycloalkyl, aryl or heterocyclic group; and the aryl and the heterocyclic group may be substituted with one or more substituents; A is $C_{1-6}$ straight-chain or branched-chain alkylene, and Y is a sulfur atom, sulfinyl or sulfonyl. The cyanomethylene compound of the invention exhibits an excellent fungicidal activity against drug resistant fungi as well as drug sensitive fungi, and can be used as a fungicide in agriculture and horticulture.

4 Claims, No Drawings

CYANOMETHYLENE COMPOUNDS, PROCESS FOR PRODUCING THE SAME, AND AGRICULTURAL OR HORTICULTURAL BACTERICIDE

FIELD OF THE INVENTION

The present invention relates to a cyanomethylene compound, a process for preparing the same and an agricultural and horticultural fungicide which contains the compound.

BACKGROUND ART

Recent years have seen the emergence of drug resistant fungi due to long term use of fungicides. For this reason, it has become difficult to accomplish control by use of known fungicides such as benzimidazole. Consequently, there is a demand for development of new type of compounds having a fungicidal activity against drug resistant fungi.

As a compound having a cyanomethylene group bonded to the 2-position on the thiazolidine ring, a compound represented by the formula (A)

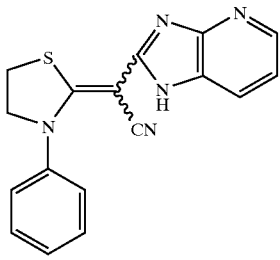

(A)

is disclosed, for example, in Phamazie, 53(6), 373–376 (1998) which reports that the compound has an antituberculous activity. However, the publication discloses nothing about the fungicidal activity of the compound of the formula (A).

WO96/33995 discloses oxopropionitrlle derivatives represented by the formula (B)

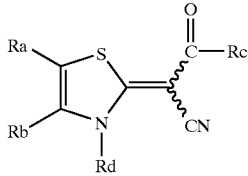

(B)

wherein Ra is an alkyl group having 2 to 8 carbon atoms, Rb is a hydrogen atom, etc., Rc is a heterocyclic group and Rd is a hydrogen atom, etc., and mentions that the derivatives have an insecticidal activity, but refers nowhere to a fungicidal activity of the derivatives.

DISCLOSURE OF THE INVENTION

An object of the invention is to provide a novel cyanomethylene compound which exhibits an excellent fungicidal activity against drug resistant fungi as well as drug sensitive fungi.

Another object of the invention is to provide a process for preparing the cyanomethylene compound.

A further object of the invention is to provide a new type of fungicide for agriculture and horticulture which exhibits a remarkable fungicidal effect against chemical-resistant fungi as well as chemical-sensitive fungi.

The invention provides cyanomethylene compounds represented by the formula (1) (hereinafter referred to as "cyanomethylene compound (1)")

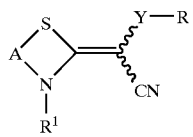

(1)

wherein R is $C_{1-20}$ straight-chain or branched-chain alkyl, $C_{3-8}$ cycloalkyl, aryl, aryl-$C_{1-4}$ alkyl or heterocyclic group; and the aryl, the aryl-$C_{1-4}$ alkyl and the heterocyclic group may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycarbonyl, $C_{1-4}$ alkylaminocarbonyl, $C_{1-4}$ alkoxyimino-$C_{1-4}$ alkyl, $C_{1-4}$ alkylamino, $C_{1-4}$ alkylcarbonyl, $C_{1-4}$ alkylthio, aryl-$C_{1-4}$ alkyl, carbamoyl, phenoxy, benzyloxy, nitro and cyano;

$R^1$ is $C_{1-8}$ straight-chain or branched-chaln alkyl, $C_{3-8}$ cycloalkyl, aryl, aryl-$C_{1-4}$ alkyl or heterocyclic group; and the aryl, the aryl-$C_{1-4}$ alkyl and the heterocyclic group may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycarbonyl, $C_{1-4}$ alkylamino, di-$C_{1-4}$ alkylamino, $C_{2-4}$ alkenyl, $C_{1-4}$ alkylthio, $C_{1-4}$ alkylsulfinyl, $C_{1-4}$ alkylsulfonyl, phenyl, phenoxy, nitro and cyano;

A is $C_{1-6}$ straight-chain or branched-chain alkylene, $C_{2-6}$ straight-chain or branched-chain alkenylene, —$CH_2$—B—$CH_2$— (wherein B is phenylene), —$CH_2$—O—B—$CH_2$— (wherein B is as defined above) or —Z—CO— (wherein Z is $C_{1-4}$ alkylene); and Y is a sulfur atom, sulfinyl or sulfonyl.

The cyanomethylene compound (1) of the invention has a broad fungicidal spectrum, and an excellent fungicidal activity of controlling chemical-resistant fungi as well as chemical-sensitive fungi.

E/Z isomers are present in the cyanomethylene compound (1) of the invention. The cyanomethylene compound (1) of the invention includes an E/Z isomer and a mixture of E/Z isomers.

The invention provides a process for preparing the cyanomethylene compound (1), the process comprising reacting:

an isothiocyanate represented by the formula (2)

$R^1$-NCS (2)

wherein $R^1$ is as defined above;

an acetonitrile represented by the formula (3)

R—Y—$CH_2$—CN (3)

wherein R and Y are as defined above, and a halogen compound represented by the formula (4)

$X^1$—A—$X^2$ (4)

wherein A is as defined above, and $X^1$ and $X^2$ are the same or different and each represents halogen atom.

The invention provides a fungicide containing the cyanomethylene compound (1) for use in agriculture and horticulture.

In the formula (1), the groups represented by each of R, $R^1$, A and Z can be exemplified as follows.

Examples of $C_{1-20}$ straight-chain or branched-chain alkyl are methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-trldecyl, n-tetradecyl, n-pentadecyl, n-hexadecyl, n-heptadecyl, n-octadecyl, n-nonadecyl and the like.

Examples of $C_{3-8}$ cycloalkyl are cyclopropyl, cyclobutyl, cyclopentyl, cyclohexyl, cycloheptyl, cyclooctyl and the like.

Examples of aryl are phenyl, naphthyl and the like.

Examples of aryl-$C_{1-4}$ alkyl are benzyl, 1-phenylethyl, 2-phenylethyl, 1-phenylpropyl, 2-phenylpropyl, 3-phenylpropyl and the like.

Examples of heterocyclic group are pyridyl, pyrimidyl, benzotriazolyl, 1,2,4-triazole-1-yl, 2-thienyl, pyrazinyl, pyridazinyl, 2-benzothiazolyl, oxazolyl, isoxazolyl, thiazolyl, 8-quinolyl, oxadiazolyl and the like.

Examples of halogen atom are fluorine, chlorine, bromine, iodine and the like.

Examples of $C_{1-4}$ alkyl are methyl, ethyl, n-propyl, isopropyl, n-butyl, isobutyl, sec-butyl, tert-butyl and like $C_{1-4}$ straight-chain or branched-chain alkyl groups.

Examples of $C_{1-4}$ haloalkyl are fluoromethyl, bromomethyl, iodomethyl, difluoromethyl, trifluoromethyl, 2-fluoroethyl, 2-chloroethyl, 1-fluoroethyl, pentafluoroethyl, 1-fluoropropyl, 2-chloropropyl, 3-fluoropropyl, 3-chloropropyl, 1-fluorobutyl, 1-chlorobutyl, 4-fluorobutyl and like straight-chain or branched-chain alkyl substituted with 1 to 9 halogen atoms.

Examples of $C_{1-4}$ alkoxy are methoxy, ethoxy, n-propoxy, isopropoxy, n-butoxy, sec-butoxy, tert-butoxy and like $C_{1-4}$ straight-chain or branched-chain alkoxy groups.

Examples of $C_{1-4}$ haloalkoxy are fluoromethoxy, chloromethoxy, bromomethoxy, iodomethoxy, difluoromethoxy, trifluoromethoxy, 2-fluoroethoxy, 2-chloroethoxy, 1-fluoroethoxy, 2,2,2-trifluoroethoxy, pentafluoroethoxy, 1-fluoropropoxy, 2-chloropropoxy, 3-fluoropropoxy, 3-chloropropoxy, 1-fluorobutoxy, 1-chlorobutoxy, 4-fluorobutoxy and like straight-chain or branched-chain alkoxy groups substituted with 1 to 9 halogen atoms.

Examples of $C_{1-4}$ alkoxycarbonyl are methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and like alkoxycarbonyl groups wherein the alkoxy moiety is $C_{1-4}$ straight-chain or branched-chain alkoxy.

Examples of $C_{1-4}$ alkylaminocarbonyl are methylaminocarbonyl, ethylaminocarbonyl, n-propylaminocarbonyl, isopropylaminocarbonyl, n-butylaminocarbonyl, isobutylaminocarbonyl, sec-butylaminocarbonyl, tert-butylaminocarbonyl and like alkylaminocarbonyl groups wherein the alkyl moiety is $C_{1-4}$ straight-chain or branched-chain alkyl.

Examples of $C_{1-4}$ alkoxyimino-$C_{1-4}$ alkyl are methoxyiminomethyl, ethoxyiminomethyl, 1-(n-propoxyimino)ethyl, isopropoxyiminomethyl, 2-(n,-butoxyimino)ethyl, sec-butoxyiminomethyl, tert-butoxyiminomethyl and like alkoxyiminoalkyl groups wherein the alkoxy moiety is $C_{1-4}$ straight-chain or branched-chain, and the alkyl moiety is $C_{1-4}$ straight-chain or branched-chain alkyl.

Examples of $C_{1-4}$ alkylamino are methylamino, ethylamino, n-propylamino, isopropylamino, n-butylamino, isobutylamino, sec-butylamino, tert-butylamino and like alkylamino groups wherein the alkyl moiety is $C_{1-4}$ straight-chain or branched-chain alkyl.

Examples of $C_{1-4}$ alkylcarobonyl are methylcarbonyl, ethylcarbonyl, n-propylcarbonyl, isopropylcarbonyl, n-butylcarbonyl, isobutylcarbonyl, sec-butylcarbonyl, tert-butylcarbonyl and like alkylcarbonyl groups wherein the alkyl moiety is $C_{1-4}$ straight-chain or branched-chain alkyl.

Examples of $C_{1-8}$ straight-chain or branched-chain alkyl are methyl, ethyl, n-propyl, isopropyl, n-butyl, isobutyl, sec-butyl, tert-butyl, n-pentyl, n-hexyl, n-heptyl, n-octyl and the like.

Examples of di-$C_{1-4}$ alkylamino group are dimethylamino, diethylamino, di-n-propylamino, diisopropylamino, di-n-butylamino, diisobutylamino, sec-butylamino, di-tert-butylamino and like dialkylamino groups wherein the alkyl moiety is $C_{1-4}$ straight-chain or branched-chain alkyl.

Examples of $C_{2-4}$ alkenyl are vinyl, allyl, 2-butenyl, 3-butenyl, 1-methylallyl and the like.

Examples of $C_{1-4}$ alkylthio are methylthio, ethylthio, n-propylthio, isopropylthio, n-butylthio, isobutylthio, sec-butylthio, tert-butylthio and like alkylthio groups wherein the alkyl moiety is $C_{1-4}$ straight-chain or branched-chain alkyl.

Examples of $C_{1-4}$ alkylsulfinyl are methylsulfinyl, ethylsulfinyl, n-propylsulfinyl, isopropylsulfinyl, n-butylsulfinyl, isobutylsulfinyl, sec-butylsulfinyl, tert-butylsulflnyl and like alkylsulfinyl groups wherein the alkyl moiety is $C_{1-4}$ straight-chain or branched-chain alkyl.

Examples of $C_{1-4}$ alkylsulfonyl are methylsulfonyl, ethylsulfonyl, n-propylsulfonyl, isopropylsulfonyl, n-butylsulfonyl, isobutylsulfonyl, sec-butylsulfonyl, tert-butylsulfonyl and like alkylsulfonyl groups wherein the alkyl moiety is $C_{1-4}$ straight-chaln or branched-chaln alkyl.

Examples of $C_{1-6}$ straight-chain or branched-chain alkylene are methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, etc.

Examples of $C_{2-6}$ straight-chain or branched-chain alkenylene are vinylidene, propylene, butenylene and the like.

Examples of $C_{1-4}$ alkylene are methylene, ethylene, trimethylene, 2-methyltrimethylene, 2,2-dimethyltrimethylene, 1-methyltrimethylene, methylmethylene, ethylmethylene, tetramethylene and the like.

Among the cyanomethylene compounds (1) of the invention, preferred are those of the formula (1) wherein R is $C_{1-20}$ straight-chain or branched-chain alkyl, $C_{3-8}$ cycloalkyl, phenyl, benzyl or heterocyclic group (the phenyl, the benzyl and the heterocyclic group may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ aLkoxycarbonyl, $C_{1-4}$ alkylaminocarbonyl, $C_{1-4}$ alkoxyimino-$C_{1-4}$ alkyl, $C_{1-4}$ alkylamino, $C_{1-4}$ alkylcarbonyl, $C_{1-4}$ alkylthio, carbamoyl, phenoxy, benzyloxy, nitro, and cyano); $R^1$ is $C_{1-8}$ straight-chain or branched-chain alkyl, $C_{3-8}$ cycloalkyl, phenyl, benzyl or pyridyl (the phenyl, the benzyl and the pyridyl may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycarbonyl, $C_{1-4}$ alkylamino, di-$C_{1-4}$ alkylamino, $C_{2-4}$ alkenyl, $C_{1-4}$ alkylthio, $C_{1-4}$ alkylsulfinyl, $C_{1-4}$ alkylsulfonyl, phenyl, phenoxy, nitro and cyano); A is $C_{1-6}$ straight-chain or branched-chain alkylene, $C_{2-4}$ straight-chain or branched-chain alkenylene, or —$CH_2$—B—$CH_2$— (wherein B is phenylene); and Y is a sulfur atom, sulfinyl or sulfonyl.

Among the cyanomethylene compounds (1) of the invention, more preferred are those of the formula (1) wherein R is phenyl (the phenyl may be substituted with at least one sustituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkylcarbonyl, $C_{1-4}$ alkylthio and cyano); $R^1$ is phenyl or pyridyl (the phenyl and the pyridyl may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycarbonyl, $C_{1-4}$ alkylamino, di-$C_{1-4}$ alkylamino, $C_{2-4}$ alkenyl, $C_{1-4}$ alkylthio, $C_{1-4}$ alkylsulfinyl, $C_{1-4}$ alkylsulfonyl, phenyl, phenoxy, nitro and cyano); A is $C_{1-6}$ straight-chain or branched-chain alkylene; and Y is a sulfur atom.

Among the cyanomethylene compounds (1) of the invention, especially preferred are those of the formula (1) wherein R is phenyl (the phenyl may be substituted with at least one substituent selected from the group consisting of halogen atom and $C_{1-4}$ haloalkyl); $R^1$ is phenyl or pyridyl (the phenyl and the pyridyl may be substituted with at least one substituent selected from the group consisting of halogen atom, $C_{1-4}$ alkyl and $C_{1-4}$ alkoxy); A is ethylene; and Y is a sulfur atom.

Among the cyanomethylene compounds (1), most preferred are those of the formula (1) wherein R is phenyl substituted with halogen atom (such as fluorine, chlorine or the like) in the 2-position of the phenyl, and with $C_{1-4}$ haloalkyl (such as trifluoromethyl) in the 5-position thereof.

Among the cyanomethylene compounds (1) of the invention, most preferred are those of the formula (1) wherein $R^1$ is phenyl unsubstituted or substituted with halogen atom (such as fluorine, chlorine or the like), $C_{1-4}$ alkyl (such as methyl) or $C_{1-4}$ alkoxy (such as methoxy) in the 2-position of the phenyl, or pyridyl unsubstituted or substituted with $C_{1-4}$ alkoxy (such as methoxy). Among the cyanomethylene compounds (1), preferred are those of the formula (1) wherein the pyridyl is 2-pyridyl or 3-pyridyl, and those of the formula (1) wherein the pyridyl is substituted with $C_{1-4}$ alkoxy (such as methoxy) in the 2-position of the pyridyl.

The cyanomethylene compound (1) of the invention can be prepared, for example, by reacting:

an isbthiocyanate represented by the formula (2)

 (2)

wherein $R^1$ is as defined above;

an acetonitrile represented by the formula (3)

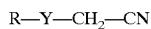 (3)

wherein R and Y are as defined above, and a halogen compound represented by the formula (4)

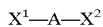 (4)

wherein A is as defined above, and $X^1$ and $X^2$ are the same or different and each represents halogen atom.

The proportions of the isothiocyanate (2) and the acetonitrile (3) to be used in the reaction are not limited and can be suitably selected from a wide range. The acetonitrile (3) is usually used in an amount of 1 to 5 moles, preferably about 1 mole or in the vicinity thereof, per mole of the isothiocyanate (2).

The proportions of the isothiocyanate (2) and the halogen compound (4) to be used in the reaction are not limited and can be suitably selected from a wide range. The halogen compound (4) is usually used in an amount of 1 to 5 moles, preferably about 1 mole or in the vicinity thereof, per mole of the isothiocyanate (2).

Preferably the reaction of the invention is carried out in the presence of a base. Useful bases are a variety of known ones, and include, for example, sodium hydrogencarbonate, sodium carbonate, potassium hydrogencarbonate, potassium carbonate, sodium hydride, potassium hydride and like inorganic bases, triethylamine, pyridine and like organic bases. These bases can be used either alone or in combination. The amount of the base to be used is not limited and can be suitably selected from a wide range. Usually the base is used in a stoichiometric amount sufficient to entrap the hydrogen halide produced by the reaction or in more than the stoichiometric amount, preferably the stoichiometric amount or about 1 to about 5 times the amount. When triethylamine, pyridine or like organic base is used, it can be used in large excess to serve also as a solvent.

The reaction of the invention is usually performed in a solvent. Useful solvents are not limited insofar as they are inert to the reaction of the invention, and include known solvents such as hexane, cyclohexane, heptane and like aliphatic or alicyclic hydrocarbons, benzene, chlorobenzene, toluene, xylene and like aromatic hydrocarbons, methylene chloride, dichloroethane, chloroform, carbon tetrachloride and like halogenated hydrocarbons, diethyl ether, tetrahydrofuran, dioxane and like ethers, dimethylformamide, dimethylsulfoxide, combinations of 2 or more thereof, etc.

The reaction of the invention is carried out usually at a temperature in the range of from –20° C. to the boiling point of the solvent used and is usually complete in about 0.5 to about 24 hours.

The raw materials used in preparing the cyanomethylene compound (1), i.e. the thiolsocyanate (2), the acetonitrile (3) and the halogen compound (4), are commercially readily available compounds or can be easily prepared by known processes.

The eyanomethylene compound (1) of the invention prepared by said process can be easily isolated from the reaction system and purified, for example, by known isolating and purifying means such as filtration, solvent extraction, distillation, recrystallization, column chromatography or the like.

The cyanomethylene compound (1) of the invention is used, for example, as an active ingredient for a fungicide.

The cyanomethylene compound (1) of the invention can be used as a fungicide by itself and can be used by being made into the desirable form such as an oil, emulsion, wettable powder, flowable preparation, granules, powder, aerosol, fumigant or the like. In this case, the content of the thiazolidine compound (1) of the invention is not limited and can be suitably selected from a wide range according to various conditions such as the form of preparation, kind of disease to be treated, kind of plant, severity of disease, place of application, time for application, method of application, chemicals to be used in combination (insecticide, nematicide, acaricide, fungicide, herbicide, plant growth control agent, synergist, soil conditioner, etc.), amount and kind of fertilizer and so on. The content is usually about 0.01 to about 95% by weight, preferably about 0.1 to about 50% by weight, based on the total amount of the fungicidal preparation.

A fungicidal preparation containing the cyanomethylene compound (1) of the invention as the active ingredient can be produced according to known processes. For example, the cyanomethylene compound (1) of the invention may be mixed with a carrier such as a solid carrier, a liquid carrier, a gaseous carrier or the like. Optionally a surfactant and other adjuvant for preparation may be added.

Useful carriers can be any of known ones which are usually used in this field.

Examples of useful solid carriers are fine particles or granules of clays (kaolin clay, diatomaceous earth, synthetic hydrated silicon dioxide, bentonite, fubasami clay, acid clay and the like), talcs, ceramics, other inorganic minerals (cerite, quartz, sulfur, activated carbon, calcium carbonate, hydrated silica, etc.), chemical fertilizers (ammonium sulfate, ammonium phosphate, ammonium nitrate, urea, ammonium chloride, etc.), and so on.

Useful liquid carriers are, for example, water, alcohols (methanol, ethanol, etc.), ketones (acetone, methyl ethyl ketone, etc.), aromatic hydrocarbons (benzene, toluene, xylene, ethylbenzene, methylnaphthalene, etc.), aliphatic hydrocarbons (hexane, cyclohexane, kerosene, light oil, etc.), esters (ethyl acetate, butyl acetate, etc.), nitriles (acetonitrile, isobutyronitrile, etc.), ethers (diisopropyl ether, dioxane, etc.), acid amides (N,N-dimethylformamide, N,N-dimethylacetamide, etc.), halogenated hydrocarbons (dichloromethane, trichloroethane, carbon tetrachloride, etc.), dimethylsulfoxide, soybean oil, cotton seed oil and like vegetable oils and so on.

Examples of useful gaseous carriers (propellants) are butane gas, LPG (liquefied petroleum gas), dimethyl ether, carbon dioxide, etc.

Examples of useful surfactants are alkyl ester sulfates, alkyl sulfonates, alkylarylsulfonates, alkyl aryl ethers, polyoxyethylenated products thereof, polyethylene glycol ethers, polyhydric alcohol esters, sugar alcohol compounds, etc.

Examples of useful adjuvants for preparation are casein, gelatin, polysaccharides (starch powder, gum arabic, cellulose compound, alginic acid, etc.), ligunin compounds, bentonite, saccharides, synthetic water-soluble polymers (polyvinyl alcohol, polyvinyl pyrrolidone, polyacrylic acid, etc.) and like fixing agents, PAP (acidic isopropyl phosphate), BBH (2,6-di-tert-butyl-4-methylphenol), BHA (mixture of 2-tert-butyl-4-methoxyphenol and 3-tert-butyl-4-methoxyphenol), vegetable oils, mineral oils, fatty acids, esters thereof and like stabilizers.

The fungicidal preparation of the invention thus obtained can be used as it is or as diluted with water. The preparation may be prepared by being mixed with any of insecticides, nematicides, acaricides, fungicides, herbicides, plant growth control agents, synergists, soil conditioners, etc. The preparation of the invention may be applied simultaneously with other preparations.

When the preparation of the invention is used as a fungicide for use in agriculture and horticulture, the amount of the preparation of the invention is not limited and can be suitably selected from a wide range according to various conditions such as the concentration of active ingredient, the form of preparation, kind of disease to be treated, kind of plant, severity of disease, time for application, method of application, chemicals to be used in combination (insecticide, nematicide, miticide, fungicide, herbicide, plant growth control agent, synergist, soil conditioner, etc.), amount and kind of a fertilizer and so on. The amount is usually about 0.001 to about 100 g per 100 $m^2$ of the area. When an emulsion, wettable powder, flowable preparation or the like is used as diluted with water, the concentration of the fungicidal preparation is about 0.1 to about 1000 ppm, preferably about 1 to 500 ppm. The granules, particles or the like are applied as such without dilution.

The compound of the invention is characterized by having an excellent fungicidal activity and a broad spectrum of activity. The compound can be used for control of plant diseases ascribed to pathogenic fungi and resistant pathogenic fungi. Examples of such pathogenic fungi include those that cause or are resistant to fungicides to treat rice plant blast, rice plant sheath blight, apple powdery mildew, apple Atternaria blotch, persimmon powdery mildew, grape powdery mildew, barley powdery mildew, wheat powdery mildew, cucumber powdery mildew, tomato late blight, strawberry powdery mildew, tobacco powdery mildew and the like.

BEST MODE FOR CARRYING OUT THE INVENTION

The invention will be described in more detail with reference to reference examples, production examples, preparation examples and test examples.

REFERENCE EXAMPLE 1

Production of 2-Fluoro-5-trifluoromethylaniline

Twenty grams of 3-nitro-4-fluorobenzotrifluoride was dissolved in 50 ml of methanol. An iron powder (16 g) was added and concentrated hydrochloric acid was added dropwise with stirring. The reaction mixture was stirred overnight, followed by addition of sodium bicarbonate for neutralization. Then diethyl ether was added, and the insolubles were filtered off with cerite. The ether phase was separated, dried and concentrated under reduced pressure, giving 14 g of the contemplated product (yield 82%).

REFERENCE EXAMPLE 2

Production of 2-Fluoro-5-trifluoromethylphenyl Thioacetonitrile

2-Fluoro-5-trifluoromethylaniline (14 g) was suspended in 30 ml of water and 10 ml of concentrated hydrochloric acid. The suspension was cooled to −5° C. while a solution of 5.93 g of sodium nitrite in 30 ml of water was added dropwise, followed by stirring at −59° C. for 2 hours. Then the solution was added to a solution of 16 g of potassium O-ethyl dithiocarbonate in 20 ml of water (40 to 50° C.), followed by stirring for 1 hour. The reaction mixture was extracted with an aqueous solution of ethyl acetate, dried and concentrated, giving 22 g of 3-ethoxythiocarbonylthio-4-fluorobenzotrifluoride.

The above-obtained 3-ethoxythiocarbonylthio-4-fluorobenzotrifluoride was dissolved in 100 ml of tetrahydrofuran without further purification. The solution was added dropwise to a suspension of 4.4 g of lithium aluminum hydride in 100 ml of tetrahydrofuran. The reaction mixture was stirred for 3 hours, followed by addition of diluted hydrochloric acid to adjust the pH to 1, and the mixture was extracted with ethyl acetate, giving 13 g of 4-fluoro-3-mercaptobenzotrifluoride.

The above-obtained 4-fluoro-3-mercaptobenzotrlfluoride was dissolved in 100 ml of acetonitrile, followed by addition of 7 g of potassium carbonate and 5 g of chloroacetonitrile. The mixture was stirred at room temperature overnight. The reaction mixture was added to water and extracted with ethyl acetate. The ethyl acetate phase was dried, concentrated and subjected to silica gel column chromatography, giving 5 g of the contemplated product (overall yield of 3 steps: 27%).

REFERENCE EXAMPLE 3

Production of (2-Fluoro-5-trifluoromethylphenylthio)-2-(3-phenylthiazolidine-2-yliden)acetonitrile 2-Fluoro-5-trifluoromethyl phenylthio-acetonitrile (0.70 g) and 0.40 g of phenylisothiocyanate were dissolved in 5 ml of dimethylformamide. To the solution stirred was added 0.25 g of 60% oil suspension of sodium hydride. The mixture was stirred with ice cooling for 0.5 hour. Then, 0.56 g of 1,2-dibromoethane was added and the mixture was stirred for 1 hour. Then 100 ml of water was added. Furthermore, 30 ml of diethyl ether was added and stirred, whereby crystals were precipitated. The crystals were filtered, giving 0.06 g of the desired product (yield 6%).

PRODUCTION EXAMPLE 1

Production of 2-(4-Chlorophenylthio)-2-(3-phenyl-1,3-thiazolidine-2 -yliden)acetonitrile (compound 1)

Dissolved in 10 ml of dimethylformamide were 1.14 g (6.7 mmols) of 4-chlorophenylisothiocyanate and 1.0 g (6.7 minols) of phenylthioacetonitrile. The solution was stirred at room temperature while 0.59 g (.60% oil, 14.8 mmols) of sodium hydride was added dropwise, followed by stirring for 1 hour. Thereto added was 1.39 g (7.4 mmols) of 1,2-dibromoethane. The mixture was stirred for 3 hours at room temperature. To the reaction mixture were added 50 ml of water and 10 ml of ether, followed by stirring. The precipitated crystals were collected by filtration, whereby 0.8 g of the title compound was obtained as colorless crystals (yield 30%).

Melting point 144–146° C.; $^1$H-NMR ($\delta$ ppm/CDCl$_3$): 3.21 (2H, t, J=7.2 Hz), 4.26 (2H, t, J=7.2 Hz), 7.1–7.5 (9H, m).

PRODUCTION EXAMPLE 2

Production of 2-Phenylthio-2-(3-phenyl-1,3-thiazolidine-2-yliden)acetonitrile (compound 2)

18.9 g (140 mmols) of phenylisothiocyanate and 20.9 g (140 mmols) of phenylthioacetonitrile dissolved in 50 ml of dimethylformamlde were added dropwise with stirring at room temperature to a suspension of 11.5 g of sodium hydride (60% oil, 287 mmols) in 200 ml of dimethylformamide. The mixture was stirred for 1 hour, and 28.9 g (154 mmols) of 1,2-dibromoethane was added dropwise at room temperature. Then the mixture was stirred for 3 hours. To the reaction mixture were added 300 ml of water and 100 ml of ether, followed by stirring. The precipitated crystals were collected by filtration, giving 26.1 g of the title compound as colorless crystals (yield 60%).

Melting point 143–145° C.; $^1$H-NMR (67 ppm/CDCl$_3$): 3.21 (2H, t, J=7.2 Hz), 4.29 (2H, t, J=7.2 Hz), 7.1–7.6 (10H, m).

Tables 1 to 7 show the compounds prepared following to the process described in Production Examples and their physical and chemical properties. In the tables, the following abbreviations mean the words shown below: OMe: methoxy group, Me: methyl group, Et: ethyl group, t-Bu: tert-butyl group, Ph: phenyl group, Bn: benzyl group, and cyc-C$_6$H$_{11}$: cyclohexyl group.

$^1$H-NMR spectrum was measured with tetramethylsilane (TMS) as the standard substance.

TABLE 1

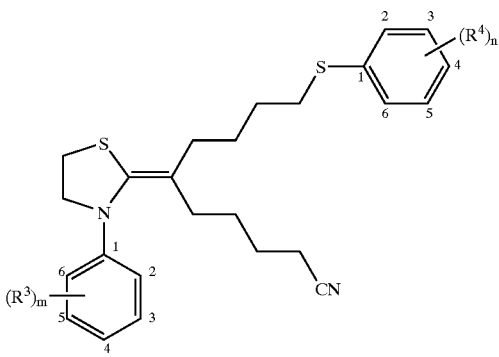

| No. | (R$^3$)$_m$ | (R$^4$)$_n$ | M.p. (° C.) | $^1$H-NMR $\delta$ppm (CDCl$_3$) |
|---|---|---|---|---|
| 3 | 2-Cl | H | 108–110 | 7.0–7.6(9H, m), 4.37 (1H, m), 4.17(1H, m), 3.27(2H, m) |
| 4 | 3-Cl | H | 118–120 | 7.1–7.5(9H, m), 4.27 (2H, t, J=7.1), 3.21 (2H, t, J=7.1) |
| 5 | 4-Me | H | 134–136 | 7.1–7.4(9H, m), 4.26 (2H, t, J=7.1), 3.19 (2H, t, J=7.1), 2.38 (3H, s) |
| 6 | 4-CF$_3$ | H | 160–162 | 7.71(2H, d, J=8.4), 7.1–7.5(7H, m), 4.30 (2H, t, J=7.1), 3.21 (2H, t, J=7.1) |
| 7 | 4-CN | H | 184–186 | 7.75(2H, d, J=8.7), 7.1–7.4(7H, m), 4.33 (2H, t, J=7.1), 3.23 (2H, t, J=7.1) |
| 8 | 4-OMe | H | 178–180 | 7.2–7.4(6H, m), 7.18 (1H, m), 6.96(2H, d, J=7.0), 4.23(2H, t, J=7.2), 3.84(3H, s), 3.19(2H, t, J=7.2) |
| 9 | 4-NO$_2$ | H | 168–170 | 8.32(2H, d, J=9.1), 7.1–7.4(7H, m), 4.37 (2H, t, J=6.9), 3.24 (2H, t, J=6.9) |
| 10 | 2-Cl 3-Cl | H | 182–184 | 7.56(1H, dd, J=7.6, 2.0), 7.1–7.4(7H, m), 4.35(1H, m), 4.13(1H, m), 3.27(2H, m) |
| 11 | 2-Cl 4-Cl | H | 154–156 | 7.55(1H, s), 7.1–7.4 (7H, m), 4.33(1H, m), 4.13(1H, m), 3.28(2H, m) |
| 12 | 2-Cl 6-Cl | H | 192–194 | 7.1–7.5(8H, m), 4.26 (2H, t, J=7.3), 3.31 (2H, t, J=7.3) |
| 13 | 3-Cl 4-Cl | H | 163–165 | 7.52(2H, d, J=8.6), 7.1–7.5(7H, m), 4.25 (2H, t, J=7.1), 3.20 (2H, t, J=7.1) |
| 14 | 3-Cl 5-Cl | H | 147–149 | 7.1–7.4(8H, m), 4.26 (2H, t, J=7.1), 3.20 (2H, t, J=7.1) |
| 15 | 2-Cl 4-Cl 6-Cl | H | 203–205 | 7.46(2H, s), 7.1–7.4 (5H, m), 4.21(2H, t, J=7.2), 3.30(2H, t, J=7.2) |
| 16 | H | 4-Cl | 105–107 | 7.1–7.6(9H, m), 4.30 (2H, t, J=7.3), 3.23 (2H, t, J=7.3) |
| 17 | 4-Cl | 4-Cl | 152–154 | 7.43(2H, d, J=8.2), 7.2–7.4(6H, m), 4.26 (2H, t, J=7.1), 3.22 (2H, t, J=7.1) |

TABLE 1-continued

| No. | (R³)ₘ | (R⁴)ₙ | M.p. (° C.) | ¹H-NMR δppm (CDCl₃) |
|---|---|---|---|---|
| 18 | H | 3-Cl | 108–110 | 7.1–7.7(9H, m), 4.32 (2H, t, J=7.2), 3.24 (2H, t, J=7.2) |
| 19 | 2-Cl | 3-Cl | 147–149 | 7.1–7.6(8H, m), 4.3–4.5(1H, m), 4.1–4.3 (1H, m), 3.2–3.4(2H, m) |
| 20 | 3-Cl | 3-Cl | 100 | 7.1–7.5(8H, m), 4.30 (2H, t, J=7.1), 3.23 (2H, t, J=7.1) |
| 21 | 4-Cl | 3-Cl | 164–166 | 7.4–7.5(2H, m), 7.1–7.4(6H, m), 4.28(2H, t, J=7.2), 3.23(2H, t, J=7.2) |
| 22 | H | 2-Cl | 96–99 | 7.2–7.6(8H, m), 7.0–7.2(1H, m), 4.32(2H, t, J=7.2), 3.22(2H, t, J=7.2) |
| 23 | 2-Cl | 2-Cl | 139–141 | 7.0–7.7(8H, m), 4.3–4.5(1H, m), 4.1–4.3 (1H, m), 3.2–3.4(2H, m) |
| 24 | 3-Cl | 2-Cl | 139–142 | 7.2–7.5(7H, m), 7.0–7.2(1H, m), 4.31(2H, t, J=7.1), 3.22(2H, t, J=7.1) |
| 25 | 4-Cl | 2-Cl | 208–210 | 7.4–7.5(2H, m), 7.2–7.4(5H, m), 7.0–7.2 (1H, m), 4.28(2H, t, J=7.2), 3.22(2H, t, J=7.2) |
| 26 | H | 4-Me | 86–88 | 7.1–7.5(9H, m), 4.28 (2H, t, J=7.3), 3.20 (2H, t, J=7.3), 2.30 (3H, s) |
| 27 | 4-Cl | 4-Me | 144–146 | 7.41(2H, d, J=8.7), 7.2–7.3(4H, m), 7.12 (2H, d, J=7.1), 4.24 (2H, t, J=7.1), 3.20 (2H, t, J=7.1), 2.32 (3H, s) |
| 28 | H | 4-MeO | 116–118 | 7.2–7.5(7H, m), 6.85 (2H, d, J=6.9), 4.26 (2H, t, J=7.1), 3.79 (3H, s), 3.21(2H, t, J=7.3) |
| 29 | 4-Cl | 4-MeO | 158–161 | 7.3–7.5(4H, m), 7.20 (2H, d, J=8.9), 6.85 (2H, d, J=2.9), 4.22 (2H, t, J=7.1), 3.79 (3H, s), 3.20(2H, t, J=7.1) |
| 30 | 2-F | H | 141–143 | 7.1–7.5(9H, m), 4.26 (2H, t, J=7.1), 3.24 (2H, t, J=7.1) |
| 31 | 2-CF₃ | H | 181–183 | 7.82(1H, d, J=7.6), 7.71(1H, dd, J=7.6, 6.8), 7.61(1H, dd, J=7.6, 6.8), 7.52(1H, d, J=7.6), 7.1–7.4 (5H, m), 4.26(2H, m), 3.35(1H, m), 3.13(1H, m) |
| 32 | 2-MeO | H | 115–117 | 7.0–7.5(9H, m), 4.30 (1H, m), 4.14(1H, m), 3.95(3H, s), 3.21(2H, m) |
| 33 | 2-Me | H | 122–124 | 7.1–7.4(9H, m), 4.22 (2H, m), 3.27(2H, m), 2.35(3H, s) |
| 34 | 4-CO₂Me | H | 170–172 | 8.13(2H, d, J=8.6), 7.2–7.4(7H, m), 4.33 (2H, t, J=7.1), 3.91 (1H, s), 3.21(2H, t, J=7.1) |
| 35 | 2-iso-C₃H₇ 6-iso-C₃H₇ | H | 208–210 | 7.44(1H, d, J=7.8), 7.1–7.5(7H, m), 4.18 (2H, t, J=7.3), 3.28 (2H, t, J=7.3), 2.98 (2H, sept, J=6.8), 1.37(6H, d, J=6.8), 1.27(6H, d, J=6.8) |
| 36 | H | 3-Me | 121–122 | 6.9–7.6(9H, m), 4.29 (2H, t, J=7.2), 3.21 (2H, t, J=7.2), 2.32 (3H, s) |
| 37 | H | 2-Me | 154–155 | 7.0–7.6(9H, m), 4.29 (2H, t, J=7.2), 3.20 (2H, t, J=7.2), 2.34 (3H, s) |
| 38 | 2-Cl | 2-Me | 177–179 | 7.0–7.8(8H, m), 4.37 (1H, m), 4.22(1H, m), 3.26(2H, m), 2.32(3H, s) |
| 39 | 2-Cl | 3-Me | 145–146 | 6.9–7.6(8H, m), 4.36 (1H, m), 4.16(1H, m), 3.26(2H, m), 2.33(3H, s) |

TABLE 1-continued

[Structure: thiazolidine with N-phenyl (R³)ₘ group, exocyclic C= bearing two chains: one (CH₂)₃-S-phenyl(R⁴)ₙ and one (CH₂)₃-CN]

| No. | (R³)ₘ | (R⁴)ₙ | M.p. (° C.) | ¹H-NMR δppm (CDCl₃) |
|---|---|---|---|---|
| 40 | H | 4-F | 132–133 | 6.9–7.6(9H, m), 4.29 (2H, t, J=7.2), 3.22 (2H, t, J=7.2) |
| 41 | H | 4-t-Bu | 134–136 | 7.1–7.5(9H, m), 4.28 (2H, t, J=7.2), 3.21 (2H, t, J=7.2) 1.30 (9H, s) |
| 42 | 3-OMe | H | 101–102 | 6.8–7.5(9H, m), 4.29 (2H, t, J=7.1), 3.84 (3H, s), 3.20(2H, t, J=7.1) |
| 43 | 3-Me | H | resin-like | 7.1–7.4(9H, m), 4.28 (2H, t, J=7.2), 3.19 (2H, t, J=7.2), 2.40 (3H, s) |
| 44 | H | 2-OMe | 170–173 | 6.8–7.6(9H, m), 4.29 (2H, t, J=7.1), 3.87 (3H, s), 3.19(2H, t, J=7.1) |
| 45 | H | 3-OMe | 82–84 | 6.7–7.6(9H, m), 4.30 (2H, t, J=7.2), 3.80 (3H, s), 3.21(2H, t, J=7.2) |
| 46 | 2-Cl | 2-OMe | 188–190 | 6.8–7.6(8H, m), 4.37 (1H, m), 4.17(1H, m), 3.87(3H, s), 3.25(2H, m) |
| 47 | 2-Cl | 3-OMe | 99–100 | 6.6–7.6(8H, m), 4.37 (1H, m), 4.17(1H, m), 3.80(3H, s), 3.27(2H, m) |

TABLE 2

[Structure: thiazolidine with N-phenyl (R³)ₘ group, exocyclic C= bearing (CH₂)₃-S-(2-naphthyl) and (CH₂)₃-CN]

| No. | (R³)ₘ | M.p. (° C.) | ¹H-NMR δppm (CDCl₃) |
|---|---|---|---|
| 48 | H | 142–143 | 7.3–7.9(12H, m), 4.31(2H, t, J=7.1), 3.22(2H, t, J=7.1) |
| 49 | 2-Cl | 150–151 | 7.3–7.8(11H, m), 4.38(1H, m), 4.19 (1H, m), 3.28(2H, m) |

TABLE 3

[Structure: thiazolidine with N-phenyl (R³)ₘ group, exocyclic C= bearing (CH₂)₃-S-(8-quinolinyl) and (CH₂)₃-CN]

| No. | (R³)ₘ | M.p. (° C.) | ¹H-NMR δppm (CDCl₃) |
|---|---|---|---|
| 50 | H | 200–201 | 7.4–9.0(11H, m), 4.34(2H, t, J=7.1), 3.22(2H, t, J=7.1) |
| 51 | 2-Cl | 199–200 | 7.3–9.0(10H, m), 4.40(1H, m), 4.21 (1H, m), 3.27(2H, m) |

TABLE 4

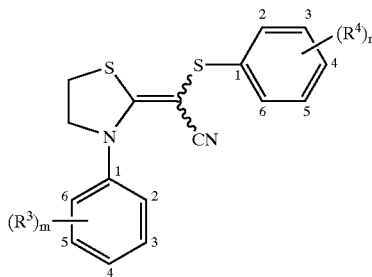

| No. | $(R^3)_m$ | $(R^4)_n$ | M.p. (° C.) | $^1$H-NMR δppm (CDCl$_3$) |
|---|---|---|---|---|
| 52 | 2-C$_2$H$_5$ | H | 136–137 | 1.3(t, J=7.6Hz, 3H), 2.5–2.9(m, 2H), 3.1–3.4(m, 2H), 4.1–4.3(m, 2H), 7.1–7.2(m, 1H), 7.2–7.5(m, 8H) |
| 53 | 2-sec-C$_4$H$_9$ | H | resin-like | 0.8–1.1(m, 3H), 1.2–1.4(m, 3H), 1.5–2.0(m, 2H), 2.7–2.9(m, 1H), 3.1–3.4(m, 2H), 4.0–4.4(m, 2H), 7.1–7.5(m, 9H) |
| 54 | 2-Br | H | 153–156 | 3.1–3.4(m, 2H), 4.1–4.3(m, 1H), 4.3–4.5(m, 1H), 7.1–7.2(m, 1H), 7.2–7.4(m, 5H), 7.4–7.5(m, 2H), 7.7(d, J=7.9Hz, 1H) |
| 55 | 2-OPh | H | resin-like | 2.8–3.3(m, 2H), 4.0–4.5(m, 2H), 6.9–7.4(m, 14H) |
| 56 | 2-OMe | 3-OMe | 133–136 | 3.1–3.4(m, 2H), 3.8(s, 3H), 4.0 (s, 3H), 4.0–4.2(m, 1H), 4.2–4.4(m, 1H), 6.7(dd, J=7.9Hz, Jm=1.4Hz, 1H), 6.8–7.0(m, 2H), 7.0–7.1(m, 2H), 7.2(t, J=7.8Hz, 1H), 7.3(dd, Jo=8.1Hz, Jm=1.4Hz, 1H), 7.3–7.5(m, 1H) |
| 57 | 2-Me | 3-OMe | 104–106 | 2.4(s, 3H), 3.1–3.4(m, 2H), 3.8 (s, 3H), 4.1–4.3(m, 2H), 6.7(dd, Jo=8.2Hz, Jm=2.2Hz, 1H), 6.8 (s, 1H), 6.9(d, J=7.7Hz, 1H), 7.2 (t, J=8.0Hz, 1H), 7.2–7.5(m, 4H) |
| 58 | H | 2-Cl<br>3-Cl | 172–175 | 3.2(t, J=7.2Hz, 2H), 4.3(t, J=7.2Hz, 2H), 7.1–7.3(m, 3H), 7.3–7.6(m, 5H) |
| 59 | 2-Cl | 2-Cl<br>3-Cl | 186–187 | 3.2–3.4(m, 2H), 4.1–4.3(m, 1H), 4.3–4.5(m, 1H), 7.1–7.3(m, 3H), 7.4–7.5(m, 3H), 7.5–7.6(m, 1H) |
| 60 | H | 2-Cl<br>5-Cl | 192–193 | 3.2(t, J=7.2Hz, 2H), 4.3(t, J=7.2Hz, 2H), 7.0–7.3(m, 3H), 7.3–7.6(m, 5H) |
| 61 | 2-Cl | 2-Cl<br>5-Cl | 184–185 | 3.2–3.4(m, 2H), 4.1–4.3(m, 1H), 4.3–4.5(m, 1H), 7.0–7.7(m, 7H) |
| 62 | H | 2-Cl<br>6-Cl | 182–183 | 3.2(t, J=7.1Hz, 2H), 4.2(t, J=7.1Hz, 2H), 7.0–7.5(m, 8H) |
| 63 | 2-Cl | 2-Cl<br>6-Cl | 172–174 | 3.2–3.4(m, 2H), 3.9–4.1(m, 1H), 4.2–4.4(m, 1H), 7.1–7.2(m, 1H), 7.3–7.4(m, 5H), 7.4–7.6(m, 1H) |
| 64 | H | 2-Me<br>5-Me | 148–150 | 2.3(s, 3H), 2.3(s, 3H), 3.2(t, J=7.1Hz, 2H), 4.3(t, J=7.1Hz, 2H), 6.9(d, J=7.1Hz, 1H), 7.0(d, J=7.6Hz, 1H), 7.1(s, 1H), 7.3–7.6 (m, 5H) |
| 65 | 2-Cl | 2-Me<br>5-Me | 175–176 | 2.3(s, 3H), 2.3(s, 3H), 3.1–3.4 (m, 2H), 4.1–4.3(m, 1H), 4.2–4.4(m, 1H), 6.9(d, J=7.2Hz, 1H), 7.0(d, J=7.6Hz, 1H), 7.2(s, 1H), 7.3–7.5(m, 3H), 7.5–7.6(m, 1H) |
| 66 | H | 3-Me<br>5-Me | 142–143 | 2.3(s, 6H), 3.2(t, J=7.1Hz, 2H), 4.3(t, J=7.1Hz, 2H), 6.8(s, 1H), 6.9(s, 2H), 7.3–7.6(m, 5H) |
| 67 | 2-Cl | 3-Me<br>5-Me | 191–193 | 2.3(s, 6H), 3.2–3.4(m, 2H), 4.1–4.3(m, 1H), 4.3–4.4(m, 1H), 6.8 |

TABLE 4-continued

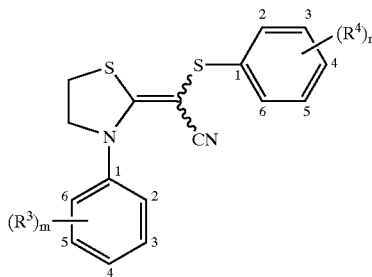

| No. | $(R^3)_m$ | $(R^4)_n$ | M.p. (° C.) | $^1$H-NMR δppm (CDCl$_3$) |
|---|---|---|---|---|
| | | | | (s, 1H), 6.9(s, 2H), 7.3–7.5(m, 3H), 7.5–7.6(m, 1H) |
| 68 | H | 3-COOMe | resin-like | 3.2(t, J=7.2Hz, 2H), 3.9(s, 3H), 4.3(t, J=7.2Hz, 2H), 7.3–7.6(m, 7H), 7.8(d, J=7.6Hz, 1H), 8.0 (d, J=1.7Hz, 1H) |
| 69 | H | 3-COOEt | resin-like | 1.4(t, J=7.1Hz, 3H), 3.2(t, J=7.2Hz, 2H), 4.3(t, J=7.2Hz, 2H), 4.4(q, J=7.1Hz, 2H), 7.3–7.6 (m, 7H), 7.8(d, J=7.7Hz, 1H), 8.0(s, 1H) |
| 70 | H | 3-n-C$_3$H$_7$ | 76–80 | 1.0(t, J=7.3Hz, 3H), 1.6–1.9 (m, 2H), 3.2(t, J=7.2Hz, 2H), 4.2–4.4(m, 4H), 7.3–7.6(m, 7H), 7.9(d, J=7.6Hz, 1H), 8.0(d, J=1.6Hz, 1H) |
| 71 | H | 3-CONHMe | resin-like | 3.0(d, J=4.8Hz, 3H), 3.2(t, J=7.2Hz, 2H), 4.3(t, J=7.2Hz, 2H), 6.1–6.2(br, 1H), 7.3–7.6(m, 8H), 7.7(s, 1H) |
| 72 | 2-Cl | 3-COOEt | 124–125 | 1.4(t, J=7.1Hz, 3H), 3.2–3.4 (m, 2H), 4.1–4.3(m, 1H), 4.3–4.5(m, 3H), 7.3–7.6(m, 6H), 7.8 (d, J=7.6Hz, 1H), 8.0(s, 1H) |
| 73 | 2-Me | 2-Cl 3-Cl | 177–178 | 2.4(s, 3H), 3.2–3.4(m, 2H), 4.2–4.3(m, 2H), 7.1–7.3(m, 3H), 7.3–7.5(m, 4H) |
| 74 | 2-OMe | 2-Cl 3-Cl | 186–187 | 3.1–3.4(m, 2H), 4.0(s, 3H), 4.1–4.3(m, 1H), 4.3–4.9(m, 1H), 7.0–7.1(m, 2H), 7.1–7.3(m, 3H), 7.3–7.4(m, 1H), 7.4–7.5(m, 1H) |
| 75 | 2-Me | 2-Cl 5-Cl | 218–220 | 2.4(s, 3H), 3.2–3.4(m, 2H), 4.2–4.4(m, 2H), 7.1(dd, Jo=8.5Hz, Jm=2.3Hz, 1H), 7.2(d, Jm=2.3Hz, 1H), 7.2(d, Jo=9.2Hz, 1H), 7.3–7.5(m, 4H) |
| 76 | 2-OMe | 2-Cl 5-Cl | 205–206 | 3.1–3.4(m, 2H), 4.0(s, 3H), 4.1–4.4(m, 2H), 7.0–7.1(m, 3H), 7.2–7.6(m, 4H) |
| 77 | 2-Me | 2-Me 5-Me | 191–193 | 2.3(s, 3H), 2.3(s, 3H), 2.4(s, 3H), 3.1–3.3(m, 2H), 4.1–4.3 (m, 2H), 6.9(d, J=7.6Hz, 1H), 7.0(d, J=7.6Hz, 1H), 7.1(s, 1H), 7.2–7.4(m, 4H) |
| 78 | 2-OMe | 2-Me 5-Me | 191–193 | 2.3(s, 3H), 2.3(s, 3H), 3.1–3.3 (m, 2H), 4.0(s, 3H), 4.0–4.2(m, 1H), 4.2–4.4(m, 1H), 6.8–6.9(m, 1H), 6.9–7.1(m, 4H), 7.3–7.5(m, 2H) |
| 79 | 2-Me | 3-Me 5-Me | 191–193 | 2.3(s, 6H), 2.4(s, 3H), 3.2–3.3 (m, 2H), 4.1–4.3(m, 2H), 6.8(s, 1H), 6.9(s, 2H), 7.2–7.4(m, 4H) |
| 80 | 2-OMe | 3-Me 5-Me | 191–193 | 2.3(s, 6H), 3.1–3.3(m, 2H), 3.9 s, 3H), 4.0–4.2(m, 1H), 4.2–4.4 m, 1H), 6.8(s, 1H), 6.9(s, 2H), 7.0–7.1(m, 2H), 7.2–7.5(m, 2H) |
| 81 | H | 3-CONH$_2$ | resin-like | 3.2(t, J=7.2Hz, 2H), 4.3(t, J=7.2Hz, 2H), 5.4–6.4(br, 2H), |

TABLE 4-continued

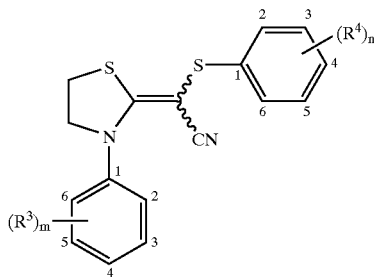

| No. | $(R^3)_m$ | $(R^4)_n$ | M.p. (° C.) | $^1$H-NMR δppm (CDCl$_3$) |
|---|---|---|---|---|
| | | | | 7.3–7.5(m, 7H), 7.6(d, J=7.5Hz, 1H), 7.5(s, 1H) |
| 82 | H | 3-CONH-n-C$_3$H$_7$ | 113–115 | 1.0(t, J=7.4Hz, 3H), 1.5–1.7(m, 2H), 3.2(t, J=7.2Hz, 2H), 3.3–3.5(m, 2H), 4.3(t, J=7.2Hz, 2H), 6.0–6.2(br, 1H), 7.3–7.6(m, 8H), 7.7(d, Jm=0.8Hz, 1H) |
| 83 | 2-Cl | 3-COOMe | 122–125 | 3.2–3.4(m, 2H), 3.9(s, 3H), 4.1–4.3(m, 1H), 4.3–4.5(m, 1H), 7.3–7.6(m, 6H), 7.8(d, J=7.6Hz, 1H), 7.9–8.1(m, 1H) |
| 84 | 2-Cl | 3-CONHMe | resin-like | 3.0(d, J=4.8Hz, 3H), 3.2–3.4(m, 2H), 4.1–4.3(m, 1H), 4.3–4.5(m, 1H), 6.0–6.2(br, 1H), 7.3–7.5(m, 5H), 7.5–7.6(m, 2H), 7.6–7.7(m, 1H) |
| 85 | 2-Cl | 3-CONHC$_2$H$_4$OMe | resin-like | 3.2–3.4(m, 2H), 3.3–3.5(m, 3H), 3.5–3.6(m, 2H), 3.6–3.7(m, 2H), 4.1–4.3(m, 1H), 4.3–4.5(m, 1H), 6.4–6.5(br, 1H), 7.3–7.5(m, 5H), 7.5–7.6(m, 2H), 7.6–7.8(m, 1H) |
| 86 | 2-Cl | 3-NH-n-C$_3$H$_7$ | resin-like | 1.0(t, J=7.4Hz, 3H), 1.5–1.8(m, 2H), 3.2–3.3(m, 2H), 3.4–3.5(m, 2H), 4.1–4.3(m, 1H), 4.3–4.5(m, 1H), 6.0–6.2(br, 1H), 7.3–7.6(m, 5H), 7.5–7.6(m, 2H), 7.6–7.7(m, 1H) |
| 87 | H | 2-Me 4-Me | 132–133 | 2.3(s, 3H), 2.3(s, 3H), 3.2(t, J=7.1Hz, 2H), 4.3(t, J=7.1Hz, 2H), 6.9–7.2(m, 2H), 7.2(d, J=7.9Hz, 1H), 7.3–7.6(m, 5H) |
| 88 | H | 2-Me 6-Me | 136–138 | 2.6(s, 6H), 3.2(t, J=7.0Hz, 2H), 4.2(t, J=7.2Hz, 2H), 7.0–7.2(m, 3H), 7.1–7.5(m, 5H) |
| 89 | 2-Ph | H | 174–175 | 2.8–3.1(m, 2H), 3.7–3.9(m, 1H), 4.0–4.2(m, 1H), 7.0–7.2(m, 3H), 7.2–7.4(m, 3H), 7.4–7.6(m, 8H) |
| 90 | 2-CN | H | 141–142 | 3.2–3.5(br, 2H), 4.2–4.6(br, 2H), 7.1–7.2(m, 1H), 7.2–7.4(m, 4H), 7.5–7.6(m, 2H), 7.7–7.9(m, 2H) |
| 91 | H | 2-Cl 4-Cl | 172–173 | 3.2(t, J=7.2Hz, 2H), 4.3(t, J=7.2Hz, 2H), 7.2(d, J=8.5Hz, 1H), 7.2–7.3(m, 1H), 7.3–7.6(m, 6H), |
| 92 | 2-iso-C$_3$H$_7$ | H | 117–119 | 1.3(d, J=6.9Hz, 3H) 1.4(d, J=6.8Hz, 3H), 3.0–3.2(m, 1H), 3.1–3.3(m, 2H), 4.1–4.3(m, 2H), 7.1–7.2(m, 1H), 7.2–7.4(m, 6H), 7.4–7.5(m, 2H) |
| 93 | 2-OEt | H | 106–110 | 1.4–1.5(m, 3H), 3.1–3.3(m, 2H), 4.0–4.3(m, 4H), 6.9–7.1(m, 3H), 7.1–7.2(m, 1H), 7.2–7.5(m, 5H) |
| 94 | 2-NO$_2$ | H | 137–138 | 3.2–3.3(m, 1H), 3.3–3.5(m, 1H), 4.1–4.3(m, 1H), 4.3–4.5(m, 1H), 7.1–7.4(m, 5H), 7.5–7.8(m, 3H), 8.1–8.2(m, 1H) |

TABLE 4-continued

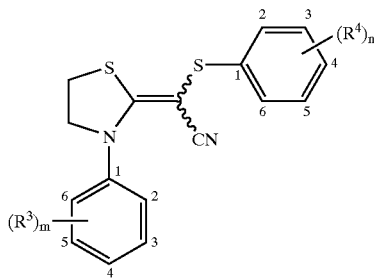

| No. | $(R^3)_m$ | $(R^4)_n$ | M.p. (° C.) | $^1$H-NMR δppm (CDCl$_3$) |
|---|---|---|---|---|
| 95 | 2-Cl<br>5-Cl | H | 125–126 | 3.1–3.4(m, 2H), 4.1–4.2(m, 1H), 4.2–4.4(m, 1H), 7.1–7.2(m, 1H), 7.2–7.5(m, 7H) |
| 96 | H | 3-F | 107–108 | 3.2(t, J=7.2Hz, 2H), 4.3(t, J=7.2Hz, 2H), 6.7–6.9(m, 1H), 6.9–7.1(m, 2H), 7.2–7.6(m, 6H) |
| 97 | H | 3-Br | 137–138 | 3.2(t, J=7.2Hz, 2H), 4.3(t, J=7.2Hz, 2H), 7.1–7.6(m, 9H) |
| 98 | H | 3-CF$_3$ | 134–135 | 3.2(t, J=7.2Hz, 2H), 4.3(t, J=7.2Hz, 2H), 7.3–7.6(m, 9H) |
| 99 | H | 3-iso-C$_3$H$_7$ | 99–100 | 1.3(d, J=6.9Hz, 6H), 2.8–3.0(m, 1H), 3.2(t, J=7.1Hz, 2H), 4.3(t, J=7.1Hz, 2H), 7.0–7.3(m, 4H), 7.3–7.6(m, 5H) |
| 100 | H | 3-Cl<br>4-Cl | resin-like | 3.2(t, J=7.2Hz, 2H), 4.3(t, J=7.2Hz, 2H), 7.1(dd, Jo=8.4Hz, Jm=2.1Hz, 1H), 7.3–7.6(m, 7H) |
| 101 | H | 2-Me<br>5-Cl | 168–169 | 2.3(s, 3H), 3.2(t, J=7.2Hz, 2H), 4.3(t, J=7.2Hz, 2H), 7.0–7.1(m, 2H), 7.2(s, 1H), 7.3–7.6(m, 5H) |
| 102 | H | 2-OMe<br>5-OMe | 134–136 | 3.2(t, J=7.1Hz, 2H), 3.8(s, 3H), 3.8(s, 3H), 4.3(t, J=7.1Hz, 2H), 6.6–6.7(m, 1H), 6.7–6.9(m, 2H), 7.3–7.5(m, 5H) |
| 103 | H | 2-Me<br>3-Me | 117–118 | 2.2(s, 3H), 2.2(s, 3H), 3.2(t, J=7.1Hz, 2H), 4.3(t, J=7.2Hz, 2H), 7.0–7.2(m, 3H), 7.3–7.5(m, 5H) |
| 104 | H | 2-OMe<br>3-OMe | resin-like | 3.2(t, J=7.1Hz, 2H), 3.9(s, 3H), 3.9(s, 3H), 4.3(t, J=7.1Hz, 2H), 6.8(d, J=8.3Hz, 1H), 6.9–7.1(m, 2H), 7.2–7.5(m, 5H) |
| 105 | H | 2-Cl<br>5-CF$_3$ | 160–161 | 3.3(t, J=7.2Hz, 2H), 4.3(t, J=7.2Hz, 2H), 7.3–7.6(m, 8H) |
| 106 | 2-n-C$_3$H$_7$ | H | 128–129 | 1.0(t, J=7.3Hz, 3H), 1.6–1.8(m, 2H), 2.4–2.8(m, 2H), 3.1–3.4(m, 2H), 4.1–4.3(m, 2H), 7.1–7.2(m, 1H), 7.2–7.5(m, 8H) |
| 107 | H | 2-F<br>5-CF$_3$ | 157–158 | 3.3(t, J=7.2Hz, 2H), 4.3(t, J=7.2Hz, 2H), 7.1–7.2(m, 1H), 7.3–7.6(m, 7H) |
| 108 | 2-CN | 2-Cl | 167–168 | 3.1–3.5(br, 2H), 4.1–4.6(br, 2H), 7.0–7.2(m, 1H), 7.2–7.4(m, 3H), 7.5–7.7(m, 2H), 7.7–7.9(m, 2H) |
| 109 | 2-CN | 3-Cl | 133–134 | 3.1–3.5(br, 2H), 4.2–4.6(br, 2H), 7.1–7.3(m, 4H), 7.5–7.6(m, 2H), 7.7–7.9(m, 2H) |
| 110 | 2-CN | 2-Cl<br>3-Cl | 223–225 | 3.1–3.5(br, 2H), 4.1–4.6(br, 2H), 7.1–7.4(m, 3H), 7.5–7.7(m, 2H), 7.7–7.9(m, 2H) |
| 111 | 2-CN | 2-Cl<br>5-Cl | 237–238 | 3.1–3.5(br, 2H), 4.1–4.6(br, 2H), 7.1(dd, Jo=8.5Hz, Jm=2.3Hz, 1H), 7.2–7.3(m, 2H), 7.5–7.7(m, 2H), 7.7–7.9(m, 2H) |
| 112 | 2-CN | 2-Me<br>5-Me | 149–150 | 2.3(s, 3H), 2.4(s, 3H), 3.1–3.5(br, 2H), 4.1–4.6(br, 2H), 6.8– |

TABLE 4-continued

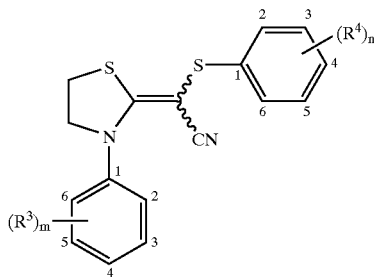

| No. | $(R^3)_m$ | $(R^4)_n$ | M.p. (° C.) | $^1$H-NMR δppm (CDCl$_3$) |
|---|---|---|---|---|
| | | | | 7.1(m, 2H), 7.2(s, 1H), 7.5–7.6 (m, 2H), 7.7–7.9(m, 2H) |
| 113 | 2-CN | 3-Me 5-Me | 167–168 | 2.2(s, 6H), 3.1–3.5(br, 2H), 4.1–4.6(br, 2H), 6.8(s, 1H), 7.0 (s, 2H), 7.4–7.6(m, 2H), 7.6–7.9(m, 2H) |
| 114 | 2-CN | 3-OMe | 150–151 | 3.2–3.5(br, 2H), 3.8(s, 3H), 4.1–4.6(br, 2H), 6.6–6.8(m, 1H), 6.8–7.0(m, 1H), 7.2–7.3(m, 1H), 7.5–7.6(m, 2H), 7.7–7.9(m, 2H) |
| 115 | H | 3-NO$_2$ | 141–142 | 3.3(t, J=7.2Hz, 2H), 4.4(t, J=7.2Hz, 2H), 7.3–7.6(m, 7H), 7.9–8.1(m, 1H), 8.1–8.2(m, 1H) |
| 116 | H | 2-OMe 3-OMe | 140–141 | 3.2(t, J=7.2Hz, 2H), 3.9(s, 3H), 3.9(s, 3H), 4.3(t, J=7.2Hz, 2H), 6.7(dd, Jo=8.1Hz, Jm=1.2Hz, 1H), 6.8(dd, Jo=8.0Hz, Jm=1.2Hz, 1H), 7.0(t, J=8.1Hz, 1H), 7.3–7.5(m, 5H) |
| 117 | H | 2-OM 4-OMe | 142–143 | 3.2(t, J=7.1Hz, 2H), 3.8(s, 3H), 3.8(s, 3H), 4.3(t, J=7.1Hz, 2H), 6.4–6.6(m, 2H), 7.2(d, J=8.4Hz, 1H), 7.2–7.5(m, 5H) |
| 118 | 2-Me | 2-F 5-CF$_3$ | 160–161 | 2.4(s, 3H), 3.2–3.4(m, 2H), 4.2–4.3(m, 2H), 7.0–7.2(m, 1H), 7.2–7.5(m, 5H), 7.5–7.6(m, 1H) |
| 119 | 2-Cl | 2-F 5-CF$_3$ | 165–166 | 3.2–3.4(m, 2H), 4.1–4.3(m, 1H), 4.3–4.5(m, 1H), 7.0–7.2(m, 1H), 7.4–7.5(m, 4H), 7.5–7.7(m, 2H) |
| 120 | 2-OMe | 2-F 5-CF$_3$ | 172–173 | 3.1–3.4(m, 2H), 4.0(s, 3H), 4.1–4.2(m, 1H), 4.3–4.4(m, 1H), 7.0–7.2(m, 3H), 7.2–7.6(m, 4H) |
| 121 | 2-CN | 2-F 5-CF$_3$ | 185–186 | 3.2–3.6(br, 2H), 4.1–4.7(br, 2H), 7.1–7.2(m, 1H), 7.4–7.7 (m, 4H), 7.7–7.9(m, 2H) |
| 122 | H | 2-Me 3-Me | 171–172 | 2.3(s, 6H), 3.2(t, J=7.1Hz, 2H), 4.3(t, J=7.1Hz, 2H), 6.9–7.2 (m, 3H), 7.7.3–7.6(m, 5H) |
| 123 | H | 3-OMe 5-OMe | 148–149 | 3.2(t, J=7.1Hz, 2H), 3.8(s, 6H), 4.3(t, J=7.1Hz, 2H), 6.2–6.3 (m, 1H), 6.4–6.5(m, 2H), 7.3–7.6(m, 5H) |
| 124 | 2-Me | 2-Cl 5-CF$_3$ | 154–155 | 2.4(s, 3H), 3.2–3.4(m, 2H), 4.2–4.4(m, 2H), 7.3–7.5(m, 7H) |
| 125 | 2-Cl | 2-Cl 5-CF$_3$ | 142–143 | 3.2–3.4(m, 2H), 4.1–4.3(m, 1H), 4.3–4.5(m, 1H), 7.3–7.5(m, 5H), 7.5–7.6(m, 2H) |
| 126 | 2-OMe | 2-Cl 5-CF$_3$ | 160–161 | 3.1–3.4(m, 2H), 4.0(s, 3H), 4.1–4.3(m, 1H), 4.3–4.5(m, 1H), 7.0–7.1(m, 2H), 7.3–7.4(m, 2H), 7.4–7.5(m, 3H) |
| 127 | 2-CN | 2-Cl 5-CF$_3$ | 188–189 | 3.1–3.5(br, 2H), 4.1–4.7(br, 2H), 7.3–7.4(m, 1H), 7.4–7.5 (m, 2H), 7.5–7.7(m, 2H), 7.7–7.9(m, 2H) |

TABLE 4-continued

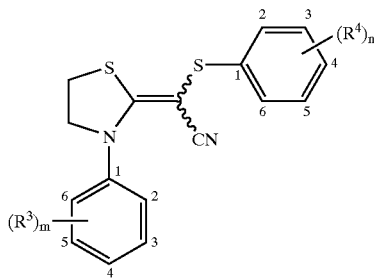

| No. | $(R^3)_m$ | $(R^4)_n$ | M.p. (° C.) | $^1$H-NMR δppm (CDCl$_3$) |
|---|---|---|---|---|
| 128 | H | 3-CH=NOMe | 112–114 | 3.2(t, J=7.2Hz, 2H), 4.0(s, 3H), 4.3(t, J=7.2Hz, 2H), 7.2–7.6(m, 9H), 8.0(s, 1H) |
| 129 | H | 3-COMe | 129–130 | 2.6(s, 3H), 3.2(t, J=7.1Hz, 2H), 4.3(t, J=7.1Hz, 2H), 7.3–7.6 (m, 7H), 7.8(t, J=7.2Hz, 1H), 7.9(s, 1H) |
| 130 | H | 3-C(Me)=NOBn | resin-like | 2.4(s, 3H), 3.1–3.3(m, 2H), 4.2–4.3(m, 2), 5.3(s, 2H), 7.2–7.5(m, 13H), 7.6(s, 1H) |
| 131 | 2-F | 2-F 5-CF$_3$ | 185–186 | 3.3(t, J=7.2Hz, 2H), 4.3(t, J=7.2Hz, 2H), 7.0–7.2(m, 1H), 7.2–7.3(m, 2H), 7.4–7.5(m, 3H), 7.5–7.6(m, 1H) |
| 132 | 2-F | 2-F 5-CF$_3$ | 180–181 | 3.3(t, J=7.2Hz, 2H), 4.3(t, J=7.2Hz, 2H), 7.2–7.6(m, 7H) |
| 133 | 2-CF$_3$ | 2-F 5-CF$_3$ | 174–175 | 3.1–3.3(m, 1H), 3.3–3.5(m, 1H), 4.1–4.4(m, 2H), 7.0–7.2(m, 1H), 7.3–7.6(m, 3H), 7.6–7.8(m, 2H), 7.8–7.9(m, 1H) |
| 134 | 2-CF$_3$ | 2-Cl 5-CF$_3$ | 173–174 | 3.1–3.3(m, 1H), 3.3–3.5(m, 1H), 4.1–4.4(m, 2H), 7.3–7.4(m, 1H), 7.4–7.5(m, 2H), 7.5–7.6(m, 1H), 7.6–7.7(m, 1H), 7.7–7.8(m, 1H), 7.8–7.9(m, 1H) |
| 135 | H | 3-Cl 5-Cl | 149–150 | 3.3(t, J=7.2Hz, 2H), 4.3(t, J=7.2Hz, 2H), 7.1–7.2(m, 3H), 7.3–7.6(m, 5H) |
| 136 | H | 3-CF$_3$ 5-CF$_3$ | 147–148 | 3.3(t, J=7.2Hz, 2H), 4.4(t, J=7.2Hz, 2H), 7.3–7.4(m, 2H), 7.4–7.6(m, 3H), 7.6–7.7(m, 3H) |
| 137 | H | 2-F 3-F 5-F 6-F | 141–142 | 3.3(t, J=7.2Hz, 2H), 4.3(t, J=7.2Hz, 2H), 6.9–7.1(m, 1H), 7.2–7.3(m, 2H), 7.3–7.5(m, 3H) |
| 138 | H | 3-Et | 106–107 | 1.2(t, J=7.6Hz, 3H), 2.6(q, J=7.6Hz, 2H), 3.2(t, J=7.1Hz, 2H), 4.3(t, J=7.1Hz, 2H), 7.0–7.1 m, 1H), 7.1–7.2(m, 2H), 7.2–7.3(m, 1H), 7.3–7.6(m, 5H) |
| 139 | 2-OCF$_3$ | 2-F 5-CF$_3$ | 149–150 | 3.2–3.4(m, 2H), 4.2–4.4(m, 2H), 7.0–7.2(m, 1H), 7.4–7.6(m, 6H) |
| 140 | 2-OCF$_3$ | 3-Cl 5-Cl | 144–145 | 3.2–3.4(m, 2H), 4.2–4.4(m, 2H), 7.1–7.2(m, 3H), 7.4–7.6(m, 4H) |
| 141 | 2-OCF$_3$ | 2-Cl 5-Cl | 165–166 | 3.2–3.4(m, 2H), 4.2–4.4(m, 2H), 7.0–7.1(m, 1H), 7.1–7.3(m, 2H), 7.4–7.6(m, 4H) |
| 142 | H | 3-OMe 5-CF$_3$ | 122–123 | 3.2(t, J=7.2Hz, 2H), 3.8(s, 3H), 4.3(t, J=7.2Hz, 2H), 6.9(s, 1H), 7.0(s, 1H), 7.1(s, 1H), 7.3–7.6 (m, 5H) |
| 143 | H | 3-F 5-F | 144–145 | 3.3(t, J=7.2Hz, 2H), 4.3(t, J=7.2Hz, 2H), 6.5–6.7(m, 1H), 6.7–6.9(m, 2H), 7.3–7.5(m, 5H) |
| 144 | 2-OCF$_3$ | H | 127–128 | 3.1–3.3(m, 2H), 4.2–4.3(m, 2H), 7.1–7.2(m, 1H), 7.2–7.3(m, 4H), 7.3–7.5(m, 4H) |

TABLE 4-continued

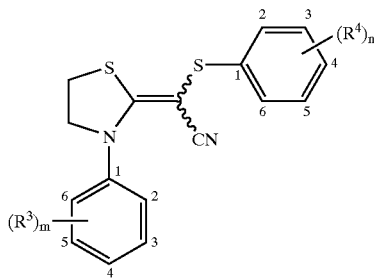

| No. | $(R^3)_m$ | $(R^4)_n$ | M.p. (° C.) | $^1$H-NMR δppm (CDCl$_3$) |
|---|---|---|---|---|
| 145 | H | 2-F<br>5-F | 149–150 | 3.3(t, J=7.2Hz, 2H), 4.3(t, J=7.2Hz, 2H), 6.7–6.9(m, 1H), 6.9–7.1(m, 2H), 7.3–7.6(m, 5H) |
| 146 | H | 5-F<br>2-Me | 150–151 | 2.3(s, 3H), 3.2(t, J=7.2Hz, 2H), 4.3(t, J=7.2Hz, 2H), 6.7–6.8(m, 1H), 6.9(dd, Jo=9.5Hz, Jm=2.6Hz, 1H), 7.0–7.1(m, 1H), 7.3–7.6(m, 5H) |
| 147 | H | 2-Cl<br>5-Me | 179–180 | 2.4(s, 3H), 3.2(t, J=7.2Hz, 2H), 4.3(t, J=7.2Hz, 2H), 6.9(dd, Jo=8.0Hz, Jm=1.7Hz, 1H), 7.0(s, 1H), 7.2(d, J=8.0Hz, 1H), 7.3–7.6(m, 5H) |
| 148 | H | 2-OMe<br>5-CF$_3$ | 181–183 | 3.2(t, J=7.2Hz, 2H), 3.9(s, 3H), 4.3(t, J=7.2Hz, 2H), 6.8–7.0(m, 1H), 7.3–7.6(m, 7H) |
| 149 | H | 2-Cl<br>5-OMe | 148–149 | 3.2(t, J=7.2Hz, 2H), 3.8(s, 3H), 4.3(t, J=7.2Hz, 2H), 6.6(dd, Jo=8.7Hz, Jm=2.8Hz, 1H), 6.8(d, Jm=2.8Hz, 1H), 7.2(d, Jo=8.7Hz, 1H), 7.3–7.6(m, 5H) |
| 150 | H | 2-F<br>5-Me | 149–150 | 2.3(s, 3H), 3.2(t, J=7.2Hz, 2H), 4.3(t, J=7.2Hz, 2H), 6.9–7.0(m, 2H), 7.1(d, J=7.1Hz, 1H), 7.3–7.6(m, 5H) |
| 151 | H | 2-OMe<br>5-Me | 175–177 | 2.3(s, 3H), 3.2(t, J=7.2Hz, 2H), 3.8(s, 3H), 4.3(t, J=7.2Hz, 2H), 6.7(d, J=8.2Hz, 1H), 6.9(d, J=8.2Hz, 1H), 7.0(s, 1H), 7.3–7.6(m, 5H) |
| 152 | H | 5-Cl<br>2-OMe | 178–180 | 3.2(t, J=7.2Hz, 2H), 3.8(s, 3H), 4.3(t, J=7.2Hz, 2H), 6.7(dd, Jo=6.9Hz, Jm=2.4Hz, 1H), 7.0–7.2(m, 2H), 7.3–7.6(m, 5H) |
| 153 | H | 2-Br<br>5-Br | 192–195 | 3.3(t, J=7.2Hz, 2H), 4.4(t, J=7.2Hz, 2H), 7.1(dd, Jo=8.4Hz, Jm=2.3Hz, 1H), 7.2–7.3(m, 1H), 7.3(d, Jm=8.4Hz, 1H), 7.3–7.6(m, 5H) |
| 154 | 2-Cl | 5-F<br>2-OMe | 211–212 | 3.2–3.4(m, 2H), 3.8(s, 3H), 4.1–4.3(m, 1H), 4.3–4.5(m, 1H), 6.6–6.9(m, 2H), 7.0(dd, Jo=8.9Hz, Jm=2.8Hz, 1H), 7.3–7.5(m, 3H), 7.5–7.6(m, 1H) |
| 155 | 2-Cl | 5-Br<br>2-Me | 175–177 | 2.2(s, 3H), 3.2–3.4(m, 2H), 4.1–4.3(m, 1H), 4.3–4.5(m, 1H), 7.0(d, J=8.0Hz, 1H), 7.2(dd, Jo=8.0Hz, Jm=1.2Hz, 1H), 7.4–7.6(m, 4H), 7.6(dd, Jo=7.3Hz, Jm=2.1Hz, 1H) |
| 156 | 2-COOMe | 2-F<br>5-CF$_3$ | 167–168 | 3.3(t, J=7.1Hz, 2H), 3.9(s, 3H), 4.4(t, J=7.1Hz, 2H), 7.2(t, J=8.8Hz, 1H), 7.4(d, J=8.5Hz, 2H), 7.4–7.5(m, 1H), 7.6(dd, Jo=6.7Hz, Jm=1.9Hz, 1H), 8.2(d, J=8.5Hz, 2H) |
| 157 | 2-SMe | H | 151–152 | 2.5(s, 3H), 3.1–3.4(m, 2H), 4.0–4.2(m, 1H), 4.3–4.4(m, 1H), 7.1– |

TABLE 4-continued

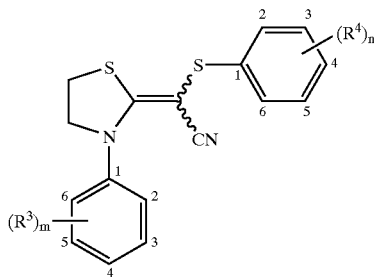

| No. | $(R^3)_m$ | $(R^4)_n$ | M.p. (° C.) | $^1$H-NMR δppm (CDCl$_3$) |
|---|---|---|---|---|
|  |  |  |  | 7.2(m, 1H), 7.2–7.4(m, 7H), 7.4–7.5(m, 1H) |
| 158 | 2-SMe | 2-F 5-CF$_3$ | 167–170 | 2.6(s, 3H), 3.1–3.3(m, 1H), 3.3–3.5(m, 1H), 4.1–4.3(m, 1H), 4.3–4.7(m, 1H), 7.0–7.2(m, 1H), 7.2–7.5(m, 5H), 7.8(dd, Jo=6.9Hz, Jm=1.9Hz, 1H) |
| 159 | 2-COOMe | H | 168–171 | 3.2–3.4(m, 2H), 3.9(s, 3H), 4.1–4.3(m, 1H), 4.4–4.6(m, 1H), 7.1–7.2(m, 1H), 7.2–7.3(m, 4H), 7.4(d, J=7.5Hz, 1H), 7.5–7.6(m, 1H), 7.6–7.7(m, 1H), 8.1(dd, Jo=7.8Hz, Jm=1.5Hz, 1H) |
| 160 | 2-SOMe | H | 199–202 | 2.9(s, 3H), 3.1–3.3(m, 1H), 3.3–3.4(m, 1H), 4.1–4.3(m, 1H), 4.4–4.5(m, 1H), 7.1–7.4(m, 5H), 7.4(dd, Jo=7.9Hz, Jm=1.1Hz, 1H), 7.6–7.8(m, 2H), 8.1(dd, Jo=7.8Hz, Jm=1.5Hz, 1H) |
| 161 | 2-SOMe | 2-F 5-CF$_3$ | 199–201 | 2.9(s, 3H), 3.3–3.5(m, 2H), 4.1–4.3(m, 1H), 4.4–4.5(m, 1H), 7.1–7.2(m, 1H), 7.4–7.5(m, 3H), 7.6–7.8(m, 2H), 8.1(dd, Jo=7.7Hz, Jm=1.6Hz, 1H) |
| 162 | 2-SO$_2$Me | H | 188–190 | 3.2(s, 3H), 3.1–3.2(m, 1H), 3.4–3.6(m, 1H), 4.0–4.2(m, 1H), 4.5–4.7(m, 1H), 7.2–7.4(m, 5H), 7.5(dd, Jo=7.8Hz, Jm=1.0Hz, 1H), 7.6–7.9(m, 2H), 8.2(dd, Jo=7.8Hz, Jm=1.5Hz, 1H) |
| 163 | 2-SO$_2$Me | 2-F 5-CF$_3$ | 154–155 | 3.2(s, 3H), 3.1–3.3(m, 1H), 3.4–3.6(m, 1H), 4.0–4.2(m, 1H), 4.6–4.8(m, 1H), 7.1–7.2(m, 1H), 7.4–7.6(m, 3H), 7.7–7.9(m, 2H), 8.2(dd, Jo=7.8Hz, Jm=1.5Hz, 1H) |
| 164 | H | 5-F 2-OMe | 178–180 | 3.2(t, J=7.2Hz, 2H), 3.8(s, 3H), 4.3(t, J=7.2Hz, 2H), 6.7–7.0(m, 3H), 7.3–7.5(m, 5H) |
| 165 | H | 5-Br 2-Me | 178–179 | 2.3(s, 3H), 3.2(t, J=7.2Hz, 3H) 4.3(t, J=7.2Hz, 2H), 7.0(d, J=8.0Hz, 1H), 7.2(dd, Jo=8.0Hz, Jm=2.0Hz, 1H), 7.3–7.6(m, 6H) |
| 166 | 2-Et | 2-F 5-CF$_3$ | 153–154 | 1.4(t, J=7.6Hz, 3H), 2.6–2.8(m, 2H), 3.2–3.4(m, 2H), 4.2–4.4(m, 2H), 7.0–7.2(m, 1H), 7.2–7.6(m, 6H), |
| 167 | 2-OEt | 2-F 5-CF$_3$ | 146–147 | 1.4(t, J=7.0Hz, 3H), 3.1–3.3(m, 2H), 4.0–4.3(m, 3H), 4.3–4.5(m, 1H), 6.9–7.2(m, 3H), 7.2–7.6(m, 4H), |
| 168 | 2-Cl 5-Cl | 2-F 5-CF$_3$ | 195–196 | 3.2–3.4(m, 2H), 4.1–4.3(m, 1H), 4.3–4.5(m, 1H), 7.1–7.3(m, 1H), 7.3–7.7(m, 5H) |
| 169 | 2-NO$_2$ | 2-F 5-CF$_3$ | 183–184 | 3.2–3.5(m, 2H), 4.2–4.3(m, 1H), 4.3–4.5(m, 1H), 7.0–7.2(m, 1H), 7.3–7.9(m, 5H), 8.2(dd, Jo=8.1Hz, Jm=1.5Hz, 1H) |
| 170 | 2-Cl | 2-F | 137–139 | 3.4(t, J=7.3Hz, 2H), 4.3(t, J= |

TABLE 4-continued

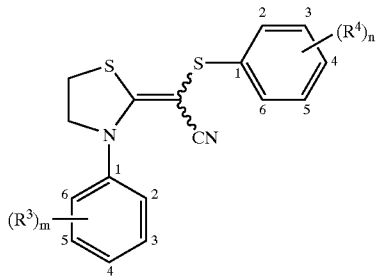

| No. | $(R^3)_m$ | $(R^4)_n$ | M.p. (° C.) | $^1$H-NMR δppm (CDCl$_3$) |
|---|---|---|---|---|
|  | 6-Cl | 5-CF$_3$ |  | 7.3Hz, 2H), 7.0–7.2(m, 1H), 7.3–7.6(m, 4H), 7.6(dd, Jo=6.9Hz, Jm=1.8Hz, 1H) |
| 171 | H | 2-Me 5-CF$_3$ | 148–150 | 2.4(s, 3H), 3.2(t, J=7.2Hz, 2H), 4.3(t, J=7.3Hz, 2H), 7.1–7.6(m, 8H) |
| 172 | H | 3-CF$_3$ | 127–128 | 3.2(t, J=7.2Hz, 2H), 4.3(t, J=7.2Hz, 2H), 7.3–7.6(m, 9H) |
| 173 | H | 3-OBn | resin-like | 3.2(t, J=1.2Hz, 2H), 4.3(t, J=7.2Hz, 2H), 5.1(s, 2H), 6.7–7.0(m, 4H), 7.1–7.7(m, 10H) |
| 174 | H | 3-OPh | 137–139 | 3.2(t, J=7.2Hz, 2H), 4.3(t, J=7.2Hz, 2H), 6.7–7.7(m, 14H) |
| 175 | 2-N(Me)$_2$ | H | 151–153 | 2.8(s, 6H), 3.1–3.3(m, 2H), 4.0–4.1(m, 1H), 4.4–4.6(m, 1H), 6.9–7.4(m, 9H) |
| 176 | 2-Me 5-OMe | H | 122–123 | 2.3(s, 3H), 3.1–3.4(m, 2H), 3.8(s, 3H), 4.1–4.3(m, 2H), 6.8(d, J=2.6Hz, 1H), 6.9(dd, Jo=8.5Hz, Jm=2.6Hz, 1H), 7.1–7.4(m, 6H) |
| 177 | 2-Cl 5-OMe | H | 159–160 | 3.1–3.4(m, 2H), 3.8(s, 3H), 4.1–4.2(m, 1H), 4.3–4.5(m, 1H), 6.9–7.0(m, 2H), 7.1–7.2(m, 1H), 7.2–7.5(m, 5H) |
| 178 | 2-OMe 5-OMe | H | 172–174 | 3.0–3.3(m, 2H), 3.8(s, 3H), 3.9(s, 3H), 4.1–4.2(m, 1H), 4.2–4.4(m, 1H), 6.9(s, 1H), 6.9–7.0(m, 2H), 7.1–7.2(m, 1H), 7.2–7.4(m, 4H) |
| 179 | 2-OMe 5-Me | H | 160–161 | 2.3(s, 3H), 3.1–3.3(m, 2H), 3.9(s, 3H), 4.1–4.2(m, 1H), 4.4(m, 1H), 6.9(d, J=8.4, 1H), 7.0–7.4(m, 7H) |
| 180 | 5-Cl 2-OMe | H | 141–142 | 3.0–3.4(m, 2H), 3.9(s, 3H), 4.0–4.4(m, 2H), 6.9(d, J=8.8Hz, 1H), 7.1–7.2(m, 1H), 7.2–7.4(m, 6H) |
| 181 | 2-Me 5-OMe | 2-F 5-CF$_3$ | 172–174 | 2.3(s, 3H), 3.2–3.4(m, 2H), 3.8(s, 3H), 4.1–4.2(m, 2H), 6.8(d, J=2.6Hz, 1H), 6.9(dd, J=8.5Hz, Jm=2.6Hz, 1H), 7.0–7.2(m, 1H), 7.2–7.3(m, 1H), 7.3–7.5(m, 1H), 7.5(dd, J=6.8Hz, Jm=2.0Hz, 1H) |
| 182 | 2-N(Me)$_2$ | 2-F 5-CF$_3$ | 172–173 | 2.9(s, 6H), 3.2–3.3(m, 2H), 4.0–4.2(m, 1H), 4.5–4.6(m, 1H), 7.0–7.2(m, 3H), 7.2–7.3(m, 1H), 7.3–7.5(m, 2H), 7.5(dd, J=6.8Hz, Jm=2.0Hz, 1H) |

TABLE 4-continued

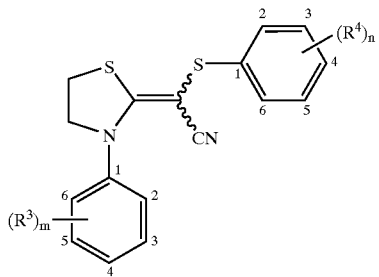

| No. | $(R^3)_m$ | $(R^4)_n$ | M.p. (° C.) | $^1$H-NMR δppm (CDCl$_3$) |
|---|---|---|---|---|
| 183 | 5-Cl<br>2-OMe | 2-F<br>5-CF$_3$ | 188–189 | 3.2–3.4(m, 2H), 3.8(s, 3H), 4.1–4.3(m, 1H), 4.3–4.5(m, 1H), 6.9–7.0(m, 2H), 7.0–7.2(m, 1H), 7.3–7.5(m, 2H), 7.7(dd, Jo=6.8Hz, Jm=1.8Hz, 1H) |
| 184 | 2-OMe<br>5-OMe | 2-F<br>5-CF$_3$ | 135–136 | 3.2–3.4(m, 2H), 3.8(s, 3H), 3.9 (s, 3H), 4.1–4.2(m, 1H), 4.3–4.5(m, 1H), 6.8–6.9(m, 1H), 6.9–7.0(m, 2H), 7.0–7.2(m, 1H), 7.3–7.5(m, 1H), 7.5(dd, Jo=6.8Hz, Jm=1.9Hz, 1H) |
| 185 | 2-OMe<br>5-Me | 2-F<br>5-CF$_3$ | 166–167 | 2.3(s, 3H), 3.1–3.4(m, 2H), 3.9 (s, 3H) 4.1–4.2(m, 1H), 4.3–4.5(m, 1H), 6.9(d, J=8.5Hz, 1H), 7.0–7.2(m, 2H), 7.2–7.3 (m, 1H), 7.3–7.5(m, 1H), 7.5 (dd, Jo=6.8Hz, Jm=2.0Hz, 1H) |
| 186 | 5-Cl<br>2-OMe | 2-F<br>5-CF$_3$ | 179–180 | 3.1–3.4(m, 2H), 3.9(s, 3H) 4.1–4.4(m, 2H), 7.0(d, J=8.9, 1H), 7.0–7.2(m, 1H), 7.2–7.5(m, 3H), 7.5(dd, Jo=6.7Hz, Jm=1.8Hz, 1H) |
| 187 | 5-Cl<br>2-Me | H | 113–114 | 2.3(s, 3H), 3.1–3.4(m, 2H), 4.1–4.3(m, 2H), 7.1–7.4(m, 8H) |
| 188 | 2-Me<br>6-Me | H | 198–199 | 2.3(s, 6H), 3.3(t, J=7.3Hz, 2H), 4.2(t, J=7.3Hz, 2H), 7.1–7.3 (m, 8H) |
| 189 | 2-F<br>6-F | H | 135–136 | 3.3(t, J=7.2Hz, 2H), 4.2(t, J=7.2Hz, 2H), 7.0–7.1(m, 2H), 7.1–7.2(m, 1H), 7.2–7.5(m, 5H) |
| 190 | 2-Me<br>6-Me | 2-F<br>5-CF$_3$ | 142–143 | 2.4(s, 6H), 3.3(t, J=7.4Hz, 2H), 4.2(t, J=7.4Hz, 2H), 7.0–7.2 (m, 3H), 7.2–7.5(m, 2H), 7.5(dd, Jo=6.8Hz, Jm=2.0Hz, 1H) |
| 191 | 2-Me<br>5-Me | H | 113–114 | 2.3(s, 3H), 2.4(s, 3H), 3.1–3.3 (m, 2H), 4.1–4.3(m, 2H), 7.1(s, 1H), 7.1–7.4(m, 7H) |
| 192 | 2-F<br>6-F | 2-F<br>5-CF$_3$ | 176–177 | 3.3(t, J=7.2Hz, 2H), 4.3(t, J=7.2Hz, 2H), 7.0–7.2(m, 3H), 7.2–7.5(m, 2H), 7.5–7.7(m, 1H) |
| 193 | 3-OMe | 2-F<br>5-CF$_3$ | 112–113 | 3.3(t, J=7.2Hz, 2H), 3.8(s, 3H), 4.3(t, J=7.2Hz, 2H), 6.8–6.9(m, 1H), 6.9–7.0(m, 2H), 7.0–7.2(m, 1H), 7.3–7.5(m, 2H), 7.5(dd, Jo=6.7Hz, Jm=2.0Hz, 1H) |

TABLE 5

| No. | R¹ | (R⁴)ₙ | M.p. (° C.) | ¹H-NMR δppm (CDCl₃) |
|---|---|---|---|---|
| 194 | 2-Methoxy-3-pyridyl | H | 165–167 | 3.1–3.3(m, 2H), 4.1 (s, 3H), 4.0–4.4(m, 2H), 6.9–7.1(m, 1H), 7.1–7.2(m, 1H), 7.2–7.4(m, 4H), 7.5–7.7(m, 1H), 8.2–8.3(m, 1H) |
| 195 | 2-Methoxy-3-pyridyl | 2-F 5-CF₃ | 159–160 | 3.1–3.4(m, 2H), 3.9–4.2(m, 1H), 4.1 (s, 3H), 4.2–4.5(m, 1H), 7.0(dd, Jo=7.5Hz, Jm=4.9Hz, 1H), 7.1(t, J=8.8Hz, 1H), 7.3–7.5(m, 1H), 7.5–7.6(m, 1H), 7.6(dd, Jo=7.5Hz, Jm=1.8Hz, 1H), 8.2–8.3(m, 1H) |
| 196 | 3-Pyridyl | H | 140–143 | 3.3(t, J=7.1Hz, 2H), 4.3(t, J=7.1Hz, 2H), 7.1–7.5(m, 6H), 7.6–7.7(m, 1H), 8.6–8.7(m, 2H) |
| 197 | 3-Pyridyl | 2-F 5-CF₃ | 140–141 | 3.3(t, J=7.1Hz, 2H), 4.4(t, J=7.1Hz, 2H), 7.1–7.2(m, 1H), 7.4–7.5(m, 2H), 7.5–7.6(m, 1H), 7.6(m, 1H), 8.0–8.7(m, 2H) |
| 198 | 5-Chloro-2-pyridyl | H | 136–139 | 3.2(t, J=7.0Hz, 2H), 4.5(t, J=7.0Hz, 2H), 7.1–7.5(m, 6H), 7.8(dd, Jo=8.7Hz, Jm=2.5Hz, 1H), 8.4 (d, J=2.5Hz, 1H) |
| 199 | 5-Chloro-3-pyridyl | 2-F 5-CF₃ | 164–165 | 3.2(t, J=7.0Hz, 2H), 4.6(t, J=7.0Hz, 2H), 7.1–7.2(m, 2H), 7.4–7.5(m, 1H), 7.7–7.8(m, 2H), 8.4(d, J=1.3Hz, 1H) |
| 200 | 6-Chloro-3-pyridyl | H | 152–154 | 3.2(t, J=7.0Hz, 2H), 4.3(t, J=7.Hz, 2H), 7.1–7.4(m, 5H), 7.4(d, J=8.5Hz, 1H), 7.6(dd, Jo=8.5Hz, Jm=2.8Hz, 1H), 8.4(d, J=2.8Hz, 1H) |
| 201 | 6-Chloro-3-pyridyl | 2-F 5-CF₃ | 150–151 | 3.3(t, J=7.0Hz, 2H), 4.3(t, J=7.1Hz, 2H), 7.1–7.3(m, 1H), 7.1–7.6(m, 3H), 7.6(dd, Jo=8.5Hz, Jm=2.8Hz, 1H), 8.4 (d, J=2.8Hz, 1H) |
| 202 | 6-Methyl-2-pyridyl | H | 125–128 | 2.6(s, 3H), 3.2(t, J=7.0Hz, 2H), 4.5(t, J=7.0Hz, 2H), 7.0–7.1(m, 2H), 7.1–7.5 (m, 5H), 7.6–7.8(m, 1H) |
| 203 | 2-Chloro-3-pyridyl | 2-F 5-CF₃ | resin-like | 3.3–3.4(m, 2H), 4.1–4.3(m, 1H), 4.3–4.7(m, 1H), 7.1–7.2(m, 1H), 7.2–7.5(m, 2H), 7.6–7.7(m, 1H), 7.7–7.9(m, 1H), 8.5–8.6(m, 1H) |
| 204 | 2-Chloro-3-pyridyl | H | 152–153 | 3.2–3.4(m, 2H), 4.1–4.2(m, 1H), 4.3–4.5(m, 1H), 7.1–7.2(m, 1H), 7.2–7.5(m, 5H), 7.8(dd, Jo=7.8Hz, Jm=1.8Hz, 1H), 8.4–8.5(m, 1H) |

TABLE 6

| No. | R¹ | Y | R | M.p. (° C.) | ¹H-NMR δppm (CDCl₃) |
|---|---|---|---|---|---|
| 205 | cyc-C$_6$H$_{11}$ | S | Ph | 124–129 | 1.0–1.3(m, 1H), 1.3–1.6(m, 4H), 1.6–1.8(m, 1H), 1.8–1.9(m, 2H), 1.9–2.1(m, 2H), 3.0(t, J=7.3Hz, 2H), 3.9(t, J=7.3Hz, 2H), 4.4–4.7(m, 1H), 7.1–7.2(m, 1H), 7.2–7.4(m, 4H) |
| 206 | tert-C$_4$H$_9$ | S | Ph | 144–146 | 1.6(s, 9H), 2.9(t, J=7.0Hz, 2H), 4.1(t, J=7.0Hz, 2H), 7.1–7.2(m, 1H), 7.3–7.4(m, 4H) |
| 207 | CH$_2$=CHCH$_2$ | S | Ph | 53–56 | 3.1(t, J=7.4Hz, 2H), 4.0(t, J=7.4Hz, 2H), 4.4–4.5(m, 2H), 5.2–5.4(m, 2H), 5.8–6.1(m, 1H), 7.1–7.2(m, 1H), 7.2–7.4(m, 5H) |
| 208 | iso-C$_3$H$_7$ | S | Ph | 91–94 | 1.3(d, J=6.5Hz, 6H), 3.0(t, J=7.3Hz, 2H), 3.9(t, J=7.3Hz, 2H), 4.9–5.1(m, 1H), 7.1–7.2(m, 1H), 7.2–7.4(m, 4H) |
| 209 | Me | S | Ph | 84–86 | 3.1(t, J=7.3Hz, 2H), 3.4(s, 3H), 4.0(t, J=7.3Hz, 2H), 7.1–7.2(m, 1H), 7.2–7.4(m, 4H) |
| 210 | Bn | S | Ph | 42–44 | 3.0(t, J=7.3Hz, 2H), 3.9(t, J=7.3Hz, 2H), 5.1(s, 2H), 7.1–7.2(m, 1H), 7.2–7.5(m, 9H) |
| 211 | Ph | S | n-C$_{16}$H$_{33}$ | 73–75 | 0.9(t, J=6.6Hz, 3H), 1.1–1.5(m, 26H), 1.5–1.7(m, 2H), 2.7(t, J=7.3Hz, 2H), 3.2(t, J=7.0Hz, 2H), 4.2(t, J=7.0Hz, 2H), 7.3–7.5(m, 5H) |
| 212 | Ph | S | n-C$_{10}$H$_{21}$ | 64–65 | 0.9(t, J=6.6Hz, 3H), 1.1–1.5(m, 14H), 1.5–1.7(m, 2H), 2.7(t, J=7.3Hz, 2H), 3.2(t, J=7.0Hz, 2H), 4.2(t, J=7.0Hz, 2H), 7.3–7.5(m, 5H) |
| 213 | Ph | S | n-C$_6$H$_{13}$ | 79–80 | 0.9(t, J=6.8Hz, 3H), 1.1–1.5(m, 6H), 1.5–1.7(m, 2H), 2.7(t, J=7.3Hz, 2H), 3.2(t, J=7.0Hz, 2H), 4.2(t, J=7.0Hz, 2H), 7.2–7.5(m, 5H) |
| 214 | Ph | S | n-C$_7$H$_{15}$ | 80–82 | 0.9(t, J=6.7Hz, 3H), 1.1–1.5(m, 8H), 1.5–1.7(m, 2H), 2.7(t, J=7.3Hz, 2H), 3.2(t, J=7.0Hz, 2H), 4.2(t, J=7.0Hz, 2H), 7.3–7.5(m, 5H) |
| 215 | 2-Chloro-phenyl | S | cyc-C$_6$H$_{11}$ | resin-like | 1.2–1.5(m, 5H), 1.5–1.6(m, 1H), 1.6–1.8(m, 2H), 1.9–2.1(m, 2H), 2.8–3.0(m, 1H), 3.1–3.4(m, 2H), 4.0–4.2(m, 1H), 4.2–4.4(m, 1H), 7.3–7.4(m, 3H), 7.4–7.6(m, 1H) |
| 216 | 2-Methyl-phenyl | S | cyc-C$_6$H$_{11}$ | 67–69 | 1.2–1.5(m, 5H), 1.5–1.6(m, 1H), 1.7–1.9(m, 2H), 1.9–2.1(m, 2H), 2.3(s, 3H), 2.8–3.0(m, 1H), 3.1–3.4(m, 2H), 4.0–4.2(m, 2H), 7.2–7.4(m, 5H) |
| 217 | 2-Cyano-phenyl | S | cyc-C$_6$H$_{11}$ | 151–152 | 1.1–1.5(m, 5H), 1.5–1.6(m, 1H), 1.7–1.9(m, 2H), 1.9–2.1(m, 2H), 2.9–3.1(m, 1H), 3.2–3.4(m, 2H), 4.1–4.4(m, 2H), 7.4–7.6(m, 2H), 7.6–7.8(m, 3H) |
| 218 | 2-Methoxy-phenyl | S | cyc-C$_6$H$_{11}$ | 102–103 | 1.2–1.5(m, 5H), 1.5–1.6(m, 1H), 1.7–1.9(m, 2H), 1.9–2.1(m, 2H), 2.8–3.0(m, 1H), 3.1–3.4(m, 2H), 3.9(s, 3H), 4.0–4.2(m, 2H), 6.9–7.1(m, 2H), 7.2–7.3(m, 2H), 7.3–7.5(m, 1H) |

TABLE 6-continued

| No. | R¹ | Y | R | M.p. (° C.) | ¹H-NMR δppm (CDCl₃) |
|---|---|---|---|---|---|
| 219 | Ph | S | Me | 103–105 | 2.3(s, 3H), 3.2(t, J=7.0Hz, 2H), 4.2(t, J=7.0Hz, 2H), 7.2–7.5(m, 5H) |
| 220 | Ph | S | Et | 87–89 | 1.3(t, J=7.4Hz, 3H), 2.7(q, J=7.4Hz, 3H), 3.2(t, J=7.0Hz, 2H), 4.2(t, J=7.0Hz, 2H), 7.2–7.5(m, 5H) |
| 221 | Ph | S | n-C₈H₁₇ | 64–66 | 0.9(t, J=6.6Hz, 3H), 1.1–1.3(m, 10H), 1.3–1.5(m, 2H), 2.7(t, J=7.3Hz, 2H), 3.2(t, J=7.0Hz, 2H), 4.2(t, J=7.0Hz, 2H), 7.3–7.5(m, 5H) |
| 222 | Ph | S | Bn | | 3.1(t, J=7.0Hz, 2H), 3.9(s, 2H), 4.1(t, J=7.0Hz, 2H), 7.1–7.5(m, 10H) |
| 223 | Ph | S | 4-Pyridyl | 115–117 | 3.3(t, J=7.2Hz, 2H), 4.3(t, J=7.2Hz, 2H), 7.1–7.2(m, 2H), 7.3–7.6(m, 5H), 8.4–8.5(m, 2H) |
| 224 | Ph | SO₂ | Ph | 197–200 | 3.3(t, J=7.5Hz, 2H), 4.2(t, J=7.5Hz, 2H), 7.1–7.3(m, 2H), 7.4–7.7(m, 6H), 7.9–8.0(m, 2H) |
| 225 | Ph | S | 3,5-Dimethyl-2-pyrimidyl | 136–138 | 2.3(s, 6H), 3.2–3.4(m, 2H), 3.4–3.5(m, 2H), 6.6(s, 1H), 7.2–7.5(m, 5H) |
| 226 | Ph | SO | Ph | 102–103 | 3.3–3.5(m, 2H), 4.1–4.4(m, 2H), 7.1–7.7(m, 10H) |
| 227 | Ph | SO | 4-Chloro-phenyl | 124–125 | 3.3–3.5(m, 2H), 4.1–4.3(m, 2H), 7.0–7.3(m, 1H), 7.3–7.7(m, 8H) |
| 228 | Ph | S | 5-Trifluoro-methyl-2-pyridyl | 175–177 | 3.2(t, J=7.2Hz, 2H), 4.3(t, J=7.2Hz, 2H), 7.3(d, J=8.5Hz, 1H), 7.4–7.6(m, 5H), 7.8(d, J=8.3Hz, 1H), 8.7(s, 1H) |
| 229 | Ph | S | 2-Benzo-thiazolyl | resin-like | 3.3–3.4(m, 2H), 3.4–3.6(m, 2H), 7.1–7.3(m, 1H), 7.3–7.4(m, 2H), 7.5–7.7(m, 2H), 7.5–7.7(m, 3H), 7.7(d, J=8.0Hz, 1H) |
| 230 | Ph | S | 2-Pyrimidyl | 147–150 | 3.2–3.4(m, 2H), 3.4–3.6(m, 2H), 6.8(t, J=4.8Hz, 1H), 7.2–7.5(m, 5H), 8.5(d, J=7.8Hz, 2H) |
| 231 | Ph | S | cyc-C₆H₁₁ | 96–97 | 1.1–1.5(m, 5H), 1.5–1.7(m, 1H), 1.7–1.9(m, 2H), 1.9–2.1(m, 2H), 2.8–3.0(m, 1H), 3.2(t, J=7.0Hz, 2H), 4.2(t, J=7.0Hz, 2H), 7.2–7.5(m, 5H) |

TABLE 7

[Structure: a thiazolidine-type ring with A-S and N-phenyl, exocyclic C=C bearing a chain with -CH2CH2CH2-S-Ph and -CH2CH2CH2-CN substituents]

| No. | A | M.p. (° C.) | ¹H-NMR δppm (CDCl3) |
|---|---|---|---|
| 232 | —CH₂—O-Ph-CH₂— | 166–167 | 3.6–3.7(m, 2H), 3.7(d, J=13Hz, 1H), 4.5(d, J=13Hz, 1H), 6.1(d, J=7.6Hz, 2H), 6.9–7.1 (m, 1H), 7.1–7.2(m, 2H), 7.2–7.5(m, 7H), 7.8(d, J=6.6Hz, 2H) |
| 233 | —CH=C(Me)— | 144–145 | 1.8(d, J=1.1Hz, 3H), 6.0(d, J=1.1Hz, 1H), 7.1–7.2(m, 1H), 7.2–7.3(m, 4H), 7.3–7.5(m, 2H), 7.5–7.7(m, 3H) |
| 234 | —CH₂C(O)— | >250 | 4.0(s, 2H), 7.1–7.2(m, 2H), 7.2–7.4(m, 2H), 7.5–7.6(m, 6H) |
| 235 | —CH₂CH(Me)— | 139–140 | 1.3(d, J=6.2Hz, 3H), 2.8–3.0(m, 1H), 3.3–3.4(m, 1H), 4.4–4.5(m, 1H), 7.1–7.2(m, 1H), 7.2–7.4(m, 6H) |
| 236 | —CH₂CH₂CH₂— | 100–102 | 2.1–2.3(m, 2H), 2.8–3.2(m, 2H), 3.8(t, J=6.2Hz, 2H), 7.0(d, J=8.2, 1H), 7.0–7.4(m, 8H), 7.4–7.5(m, 1H) |

Given below are Preparation Examples in which the parts are all by weight.

PREPARATION EXAMPLE 1 (EMULSION)

Ten parts of each compound of the invention prepared above was dissolved in 45 parts of Solvesso 150 and 35 parts of N-methylpyrrolidone. Ten parts of Sorpol 3005 X (emulsifier, product of Toho Chemical Industry Co., Ltd.) was added to the solution. The mixture was stirred, giving 10% emulsions of each compound.

PREPARATION EXAMPLE 2 (WETTABLE POWDER)

Twenty parts of each compound of the invention was added to a mixture of 2 parts of sodium lauryl sulfate, 4 parts of sodium lignin sulfonate, 20 parts of fine particles of synthetic hydrated silicon dioxide and 54 parts of clay. The mixture was stirred by a juice mixer, giving 20% wettable powders of each compound.

PREPARATION EXAMPLE 3 (GRANULES)

Five parts of each compound of the invention was mixed with 2 parts of sodium dodecylbenzene sulfonate, 10 parts of bentonite and 83 parts of clay, and sufficiently stirred. A suitable amount of water was added to the mixture. The mixture was further stirred and granulated by a granulator. The granules were air-dried, giving 5% granules of each compound.

PREPARATION EXAMPLE 4 (POWDER)

One part of each compound of the invention was dissolved in an appropriate amount of acetone. Added thereto were 5 parts of fine particles of synthetic hydrated silicon dioxide, 0.3 part of acidic isopropyl phosphate (PAP) and 93.7 parts of clay. The mixture was stirred by a juice mixer and acetone was removed by vaporization, giving 1% powders of each compound.

PREPARATION EXAMPLE 5 (FLOWABLE PREPARATION)

Mixed together were 20 parts of each compound of the invention, and 20 parts of water containing 3 parts of polyoxyethylene tristyrylphenylether phosphoric acid ester triethanolamine and 0.2 part of RHODORSIL 426 R. The mixture was subjected to wet pulverization using Dynomill, and was mixed with 60 parts of water containing 8 parts of propylene glycol and 0.32 part of xanthane gum, whereby 20% aqueous suspensions of each compound were obtained.

Test Examples are given below to show that the compound of the invention is useful as the effective ingredient for a fungicide.

Test Example 1 (Fungicidal Test for Control of Cucumber Powdery Mildew)

A methanol solution of the test compound was mixed with an aqueous solution (100 ppm) of Sorpol 355 (product of Toho Chemical Industry Co., Ltd.), giving a sample solution (200 ppm). The sample solution was spread over cucumber (14 days after seeding) planted in a pot (7.5 cm in diameter), and afr-dried. A suspension containing spores of cucumber powdery mildew (1.0 mm X $10^5$ cells/ml) was sprayed over the plant by a spray gun. After air-drying, the plant was left to stand In a house made of acrylic resin sheet and after 10 days checked for the severity of disease. The percent disease control value was calculated, compared with the severity of disease in untreated plant.

The test was carried out using the sample solutions of the compound under the following compound numbers (indicated in the tables): 2, 3, 12, 18, 22, 23, 31, 32, 33, 45, 52, 56–61, 64–67, 74–80, 90, 93–99, 101, 102, 105, 107, 109, 112–114, 118–122, 124–127, 131–139, 142–147, 150, 157–159, 161, 165–172, 179, 181–188, 190–195, 203, 204, 216, 218 and 231. The test results show that each compound exhibited a percent disease control value of 50% or more.

Test Example 2 (Fungicidal Test for Controlling of Wheat Powdery Mildew)

Aisai No.1 (JA) was packed in a pot for growing a plug seedling (trade name "Naesaku-kun, product of Kobayashi Co., Ltd., each hole measuring 30 mm in length, 30 mm in width and 40 mm in depth, 136 holes), and wheat seeds (species of wheat: "Shirasagi") were sown, and were grown in a glass house for 7 days. A test solution (200 ppm) was prepared by adding a suitable amount of methanol solution of the compound of the invention (4000 ppm) to a 500-fold diluted solution of Panguard KS-20. Wheat seedlings were placed in a cylindrical container of 24 cm in diameter laid on a turn table. The test solution was applied to the inside of the cyllndrial container using a spray gun (product of Olympos Co., Ltd., PB-408, provided with a flat nozzle cap), 1.5 kgf/cm². After air-drying, wheat (species "Shrasagi") having powdery mildew pathogen (Erysiphe graminis f. sp. tritilci) cultivated by subculture was shaken over the plant to sprinkle the conidia over the plant. The container was placed in a temperature controlled chamber (18° C., fluorescent light shining for 12 hours) for 7 days. The severity of disease in the first leaf was evaluated by scores from zero (no symptom) to 10 (development of disease throughout the leaf).

The percent disease control value was obtained by calculation of the following equation, compared with the severity of disease in untreated plants:

$$\text{Percent disease value} = \frac{1 - \text{severity of disease in treated plant}}{\text{severity of disease in untreated plant}} \times 100$$

The test was carried out using the test solutions of the compound of the invention under the following compound numbers (shown in the tables): 42, 58, 60, 64, 66, 67, 98, 105, 107, 118, 119, 159, 171, 185, 195 and 231. The test results show that each compound exhibited a percent disease control value of 50% or more.

What is claimed is:

1. A cyanomethylene compound represented by the formula (1)

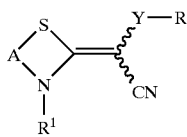

(1)

wherein R is phenyl; and the phenyl may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkyloarbonyl, $C_{1-4}$ alkylthio and cyanoa;

$R^1$ in phenyl or pyridyli and the phenyl and the pyridyl may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycarbonyl$_{1-4}$ alkylamino, di-$C_{1-4}$ alkylamino, $C_{2-4}$ alkenyl, $C_{1-4}$ alkylthio, $C_{1-4}$ alkylsulfinyl, $C_{1-4}$ alkylsulfonyl, phenyl, phenoxy, nitro and cyano;

A is $C_{1-6}$ straight-chain or branched-chain akylene; and

Y in a sulfur atom.

2. The cyanomethylene compound according to claim 1, wherein R is phenyl; and the phenyl may be substituted with at least one substituent selected from the group consisting of nalogen atom and $C_{1-4}$ haloalkyl; $R^1$ phenyl or pyridyl; and the phenyl and the pyridyl may be substituted with at least one substituent selected from the group consisting of halogen atom, $C_{1-4}$ alkyl and $C_{1-4}$ alkoxy; A is ethylene; and Y is a sulfur atom.

3. A process for preparing a cyanomethylene compound represented by the formula (1)

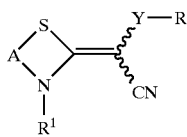

(1)

wherein R is phenyl; and the phenyl may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkylcarbonyl, $C_{1-4}$ alkylthio and cyano;

$R^1$ is phenyl or pyridyl; and the phenyl and the pyridyl may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycarbonyl, $C_{1-4}$ alkylamino, di-$C_{1-4}$ alkylamino, $C_{2-4}$ alkenyl, $C_{1-4}$ alkylthio, $C_{1-4}$ alkylsulfinyl, $C_{1-4}$ alkylsulfonyl, phenyl, phenoxy, nitro and cyano;

A is $C_{1-6}$ straight-chain or branched-chain alkylene; and

Y is a sulfur atom, the process comprising reacting:

an isothiocyanate represented by the formula (2)

$$R^1\text{---NCS} \quad (2)$$

wherein $R^1$ in as defined above;

an acetonitrile represented by the formula (3)

$$R\text{---}Y\text{---}CH_2\text{---}CN \quad (3)$$

wherein R and Y are as defined above, and a halogen compound represented by the formula (4)

$$X^1\text{---}A\text{---}X^2 \quad (4)$$

wherein A is as defined above, and $X^1$ and $X^2$ are the same or different and each represents halogen atom.

4. A fungicide useful in agriculture and horticulture, which contains a cyanomethylene comnpound of formula (1) represented by the formula (1)

(1)

wherein R is $C_{1-20}$ straight-chain or branched-chain alkyl, $C_{3-8}$ cycloalkyl, aryl, aryl-$C_{1-4}$ al or heterocyclic group; and the aryl, the aryl-$C_{1-4}$ alkyl and the heterocyclic group may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycabonyl, $C_{1-4}$ alkylminocarbonyl, $C_{1-4}$ alkoxyimino-$C_{1-4}$ alkyl, $C_{1-4}$ alkylamino, $C_{1-4}$ alkyocarbonyl, $C_{1-4}$ alkylthio, aryl-$C_{1-4}$ alkyl, carbamoyl, phenoxy, benzyloxy, nitro and cyano;

$R^1$ is $C_{1-8}$ straight-chain or branch d-chain alkyl, $C_{3-8}$ cycloalkyl, aryl, aryl-$C_{1-4}$ alkyl or heterocyclic group; and the aryl, the aryl-$C_{1-4}$ alkyl and the hetrocyclic group may be substituted with at least one substituent selected from the group consisting of halogen atom, $C_{1-4}$ alkyl, $C_{1-4}$ haloakyl, $C_{1-4}$ alhoxy, $C_{1-4}$ haloalkoxy, $C_{1-4}$ alkcoxycarbonyl, $C_{1-4}$ alkylamino, di-$C_{1-4}$ alkylamino, $C_{2-4}$ alkenyl, $C_{1-4}$ alkylthio, $C_{1-4}$ alkylsulfinyl, $C_{1-4}$ alkylsulfonyl, phenyl, phenoxy, nitro and cyano;

A is $C_{1-6}$ straight-chain or branched-chain alkylene, $C_{2-6}$ straight-chain or branched-chain alkenylene, —$CH_2$—B—$CH_2$— (wherein B Is phenylene), —$CH_2$—O—B—$CH_2$— (wherin B is an defined above) or —Z—CO— (wherein Z is $C_{1-4}$ alkylene); and Y is a sulfur atom, sulfinyl or sulfonyl.

* * * * *

UNITED STATES PATENT AND TRADEMARK OFFICE
CERTIFICATE OF CORRECTION

PATENT NO. : 6,710,062 B1
DATED : March 23, 2004
INVENTOR(S) : Hayashi et al.

It is certified that error appears in the above-identified patent and that said Letters Patent is hereby corrected as shown below:

Title page,
Item [54], Title, change "[54] CYANOMETHYLENE COMPOUNDS, PROCESS FOR PRODUCING THE SAME, AND AGRICULTURAL OR HORITCULTURAL BACTERICIDE" to -- [54] CYANOMETHYLENE COMPOUNDS, PROCESS FOR PRODUCING THE SAME, AND FUNGICIDE FOR AGRICULTURE OR HORTICULTURE --
Item [56], References Cited, FOREIGN PATENT DOCUMENTS, change
"DE    227705 Al    9/1985
 DE    240544 Al    11/1986" to
-- DD    227705 Al    9/1985
 DD    240544 Al    11/1986 --
Item [57], ABSTRACT, change "substltuents); $R^1$" to -- substituents); $R^1$ -- also change "sulflnyl or sulfonyl." to -- sulfinyl or sulfonyl --

Column 43,
Lines 34 and 35, change "cyanoa; $R^1$ in phenyl or pyridyli" to -- cyano; $R^1$ is phenyl or pyridyl --
Line 39, change alkoxycarbonyl$_{1-4}$ to -- alkoxycarbonyl $C_{1-4}$ --
Line 43, change "Y in a sulfur atom" to -- Y is a sulfur atom --
Line 47, change "nalogen atom to -- halogen atom --

Column 44,
Line 15, change "$R^1$ in" to -- $R^1$ is --
Line 28, change "comnpound" to -- compound --
Line 29, change "(1) represented by the formula (1)" to -- (1) represented --
Line 40, change "aryl-$C_{1-4}$ al" to -- aryl-$C_{1-4}$ alkyl --
Line 45, change "alkylminocarbonyl, $C_{1-4}$" to -- alkylaminocarbonyl, $C_{1-4}$ --
Line 46, change "$C_{1-4}$ alkyocarbonyl, to -- $C_{1-4}$ alkylcarbonyl --
Line 48, change "branch d-chain alkyl, $C_{3-8}$" to -- branched chain, $C_{3-8}$ --
Line 53, change "$C_{1-4}$ alhoxy" to -- $C_{1-4}$ alkoxy --
Line 54, change "alkcoxycarbonyl" to -- alkoxycarbonyl --
Line 60, change "B Is" to -- B is --
Line 64, insert claims 5 and 6 as follows:
5. The fungicide for use in agriculture and horticulture which contains the cyanomethylene compound as defined in claim 1 or 2.

UNITED STATES PATENT AND TRADEMARK OFFICE
CERTIFICATE OF CORRECTION

PATENT NO. : 6,710,062 B1
DATED : March 23, 2004
INVENTOR(S) : Hayashi et al.

It is certified that error appears in the above-identified patent and that said Letters Patent is hereby corrected as shown below:

Column 44 (cont'd),

6. Use of, as a fungicide for agriculture and horticulture, a cyanomethylene compound represented by the formula (1)

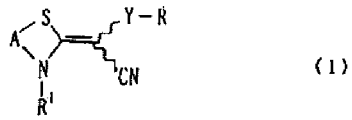

(1)

wherein R is $C_{1-20}$ straight-chain or branched-chain alkyl, $C_{3-8}$ cycloalkyl, aryl, aryl-$C_{1-4}$ alkyl or heterocyclic group; and the aryl, the aryl-$C_{1-4}$ alkyl and the heterocyclic group may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycarbonyl, $C_{1-4}$ alkylaminocarbonyl, $C_{1-4}$ alkoxyimino-$C_{1-4}$ alkyl, $C_{1-4}$ alkylamino, $C_{1-4}$ alkylcarbonyl, $C_{1-4}$ alkylthio, aryl-$C_{1-4}$ alkyl, carbamoyl, phenoxy, benzyloxy, nitro and cyano;

$R^1$ is $C_{1-8}$ straight-chain or branched-chain alkyl, $C_{3-8}$ cycloalkyl, aryl, aryl-$C_{1-4}$ alkyl or heterocyclic group; and the aryl, the aryl-$C_{1-4}$ alkyl and the heterocyclic group may be substituted with at least one substituent selected from the group consisting of halogen atom, $C_{1-4}$ alkyl, $C_{1-4}$ haloalkyl, $C_{1-4}$ alkoxy, $C_{1-4}$ haloalkoxy, $C_{1-4}$ alkoxycarbonyl, $C_{1-4}$ alklamino, di-$C_{1-4}$ alkylamino, $C_{2-4}$ alkenyl, $C_{1-4}$ alkythio, $C_{1-4}$ alkysulfinyl, $C_{1-4}$ alkylsulfonyl, phenyl, phenoxy, nitro and cyano;

A is $C_{1-6}$ straight-chain or branched-chain alkylene, $C_{2-6}$ straight-chain or branched-chain alkenylene, $-CH_2-B-CH_2$ (wherein B is phenylene), $-CH_2-O-B-CH_2-$ (wherein B is as defined above) or $-Z-CO-$ (wherein Z is $C_{1-4}$ alkylene); and
Y is a sulfur atom, sulfinyl or sulfonyl.

Signed and Sealed this

Twenty-sixth Day of July, 2005

JON W. DUDAS
*Director of the United States Patent and Trademark Office*